(12) United States Patent
Crandall

(10) Patent No.: US 10,254,077 B2
(45) Date of Patent: Apr. 9, 2019

(54) SELF-DEFENSE SYSTEM

(71) Applicant: Crandall Technologies LLC, Reno, NV (US)

(72) Inventor: Jerry Alan Crandall, Reno, NV (US)

(73) Assignee: Crandall Technologies LLC, Reno, NV (US)

( * ) Notice: Subject to any disclaimer, the term of this patent is extended or adjusted under 35 U.S.C. 154(b) by 227 days.

(21) Appl. No.: 15/346,710

(22) Filed: Nov. 8, 2016

(65) Prior Publication Data
US 2017/0051998 A1    Feb. 23, 2017

Related U.S. Application Data

(62) Division of application No. 14/280,542, filed on May 16, 2014, now abandoned, and a division of application No. 13/181,467, filed on Jul. 12, 2011, now Pat. No. 8,854,789.

(51) Int. Cl.
| | | |
|---|---|---|
| F41B 15/04 | (2006.01) | |
| F41H 9/10 | (2006.01) | |
| F41H 13/00 | (2006.01) | |
| A61B 5/024 | (2006.01) | |
| G08C 19/00 | (2006.01) | |
| H04W 4/02 | (2018.01) | |
| G08C 17/02 | (2006.01) | |

(52) U.S. Cl.
CPC .......... *F41B 15/04* (2013.01); *A61B 5/02438* (2013.01); *F41H 9/10* (2013.01); *F41H 13/0012* (2013.01); *F41H 13/0018* (2013.01); *F41H 13/0025* (2013.01); *F41H 13/0081* (2013.01); *G08C 19/00* (2013.01); *G08C 17/02* (2013.01); *H04W 4/02* (2013.01)

(58) Field of Classification Search
USPC ................................................. 361/230, 232
See application file for complete search history.

(56) References Cited

U.S. PATENT DOCUMENTS

| | | | | |
|---|---|---|---|---|
| 5,289,164 A | * | 2/1994 | Novak | ........................ F41H 9/10 116/DIG. 44 |
| 5,484,085 A | * | 1/1996 | Bennett | ...................... F41H 9/10 222/175 |
| 5,673,436 A | * | 10/1997 | Piper | ................ A41D 19/01594 2/160 |
| 7,221,552 B1 | * | 5/2007 | Brown | ....................... F41H 5/08 361/232 |
| 7,477,504 B1 | | 1/2009 | Delida | |
| 2004/0264099 A1 | | 12/2004 | Sikes | |
| 2005/0039499 A1 | | 2/2005 | Didomenico | |
| 2011/0120388 A1 | | 5/2011 | Shahbaz | |

* cited by examiner

*Primary Examiner* — Danny Nguyen
(74) *Attorney, Agent, or Firm* — Jerry A. Crandall, Esq.

(57) ABSTRACT

In an embodiment, a self-defense system is disclosed. The self-defense system may include or comprise a material sized to conform to an appendage, and a defense unit coupled with the material and positioned to initiate a defense event in response to an input.

20 Claims, 39 Drawing Sheets

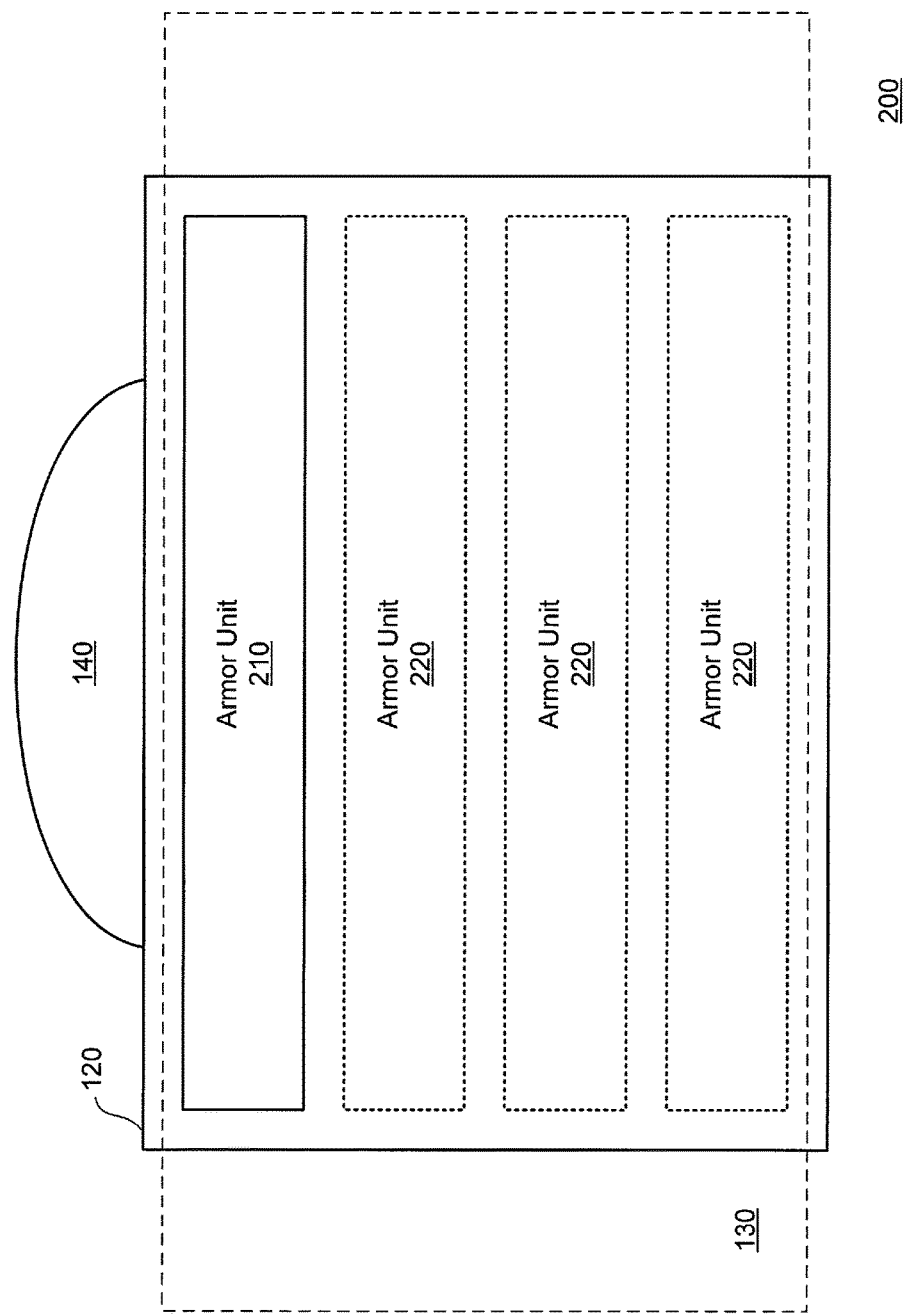

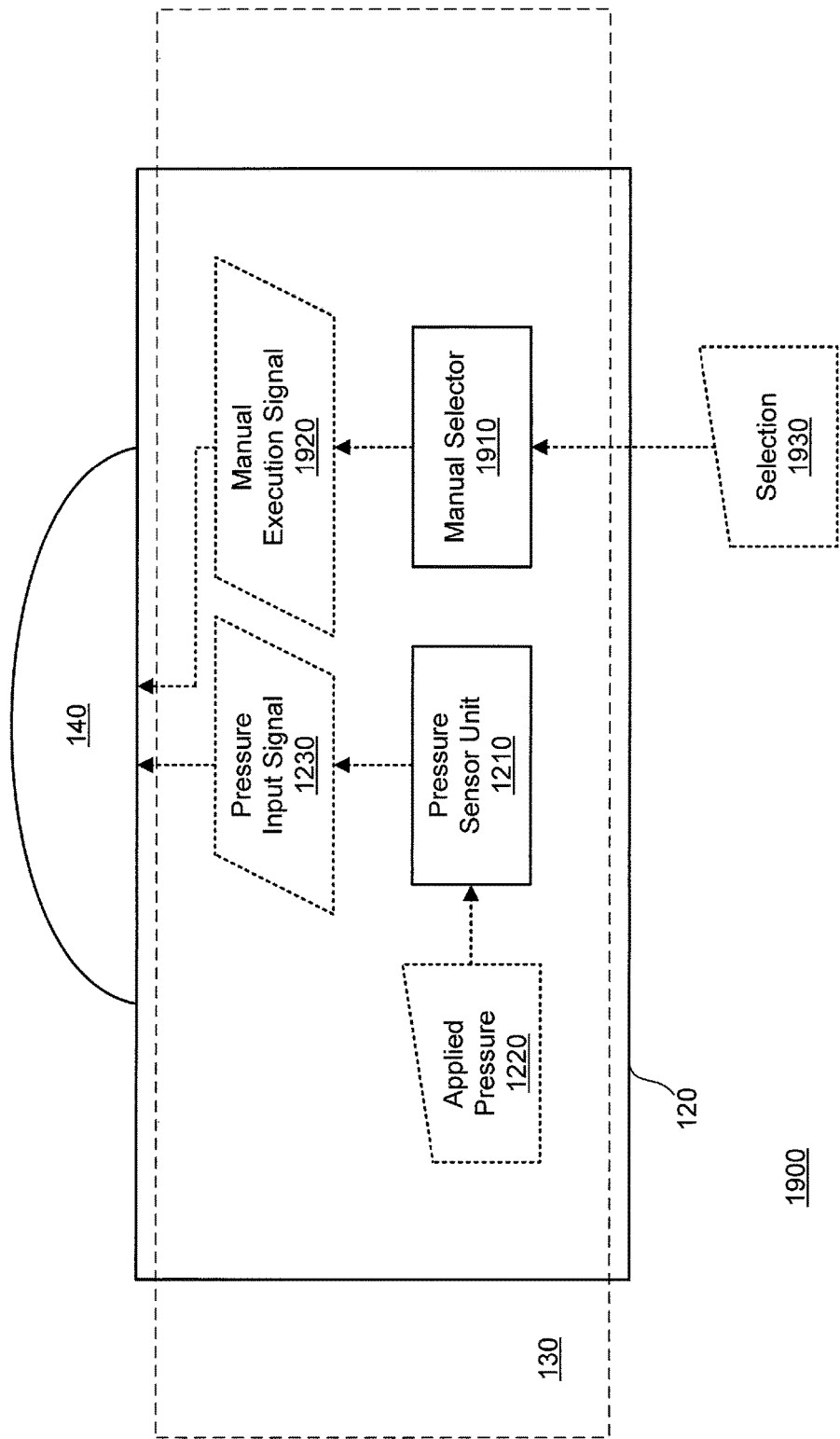

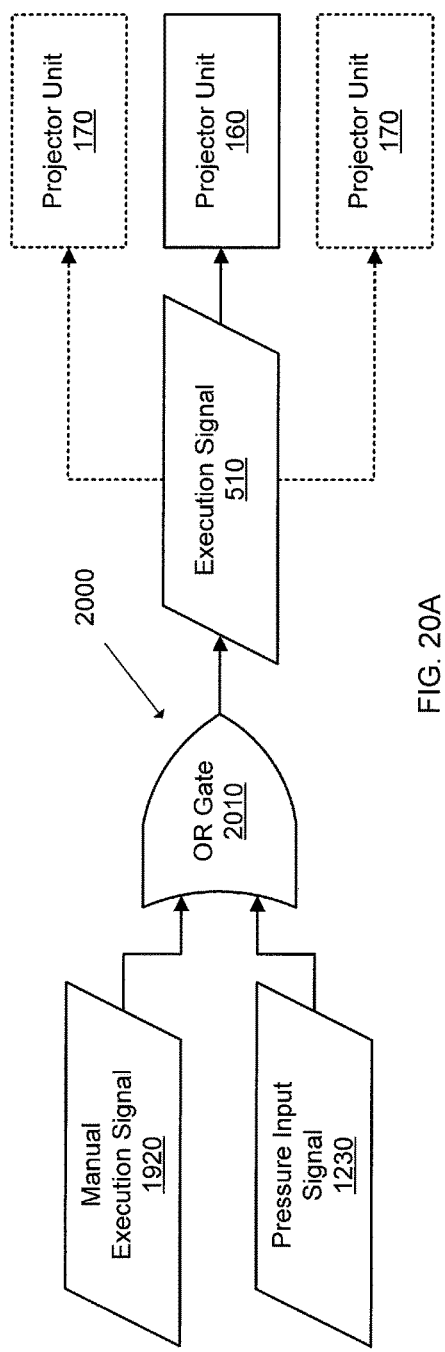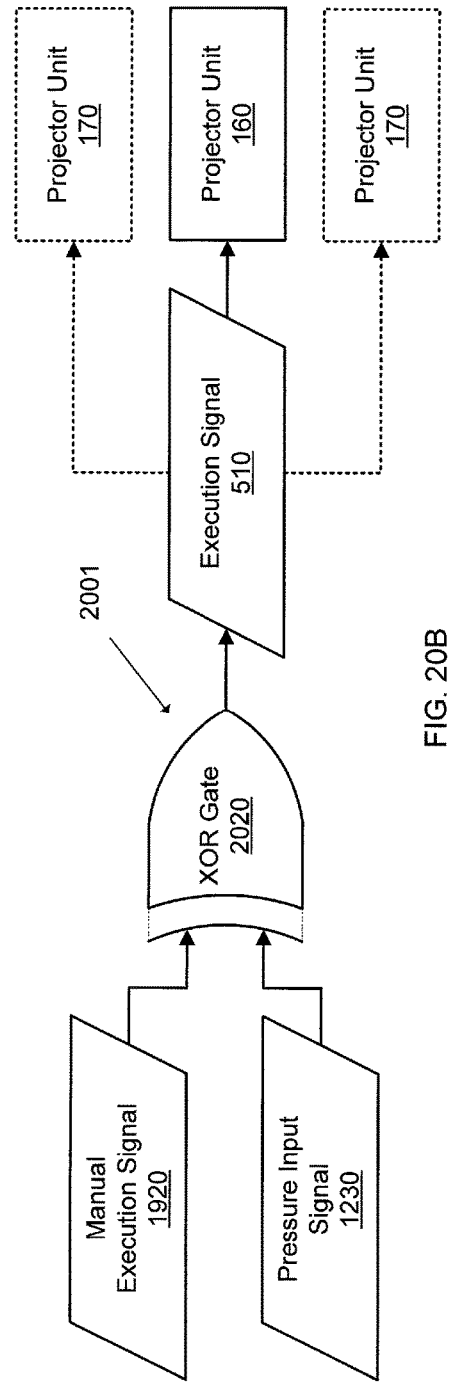

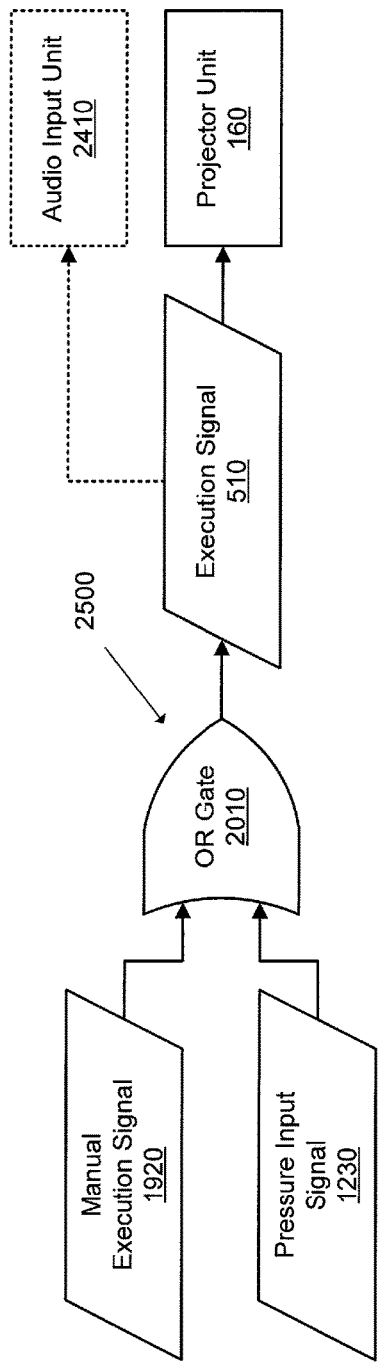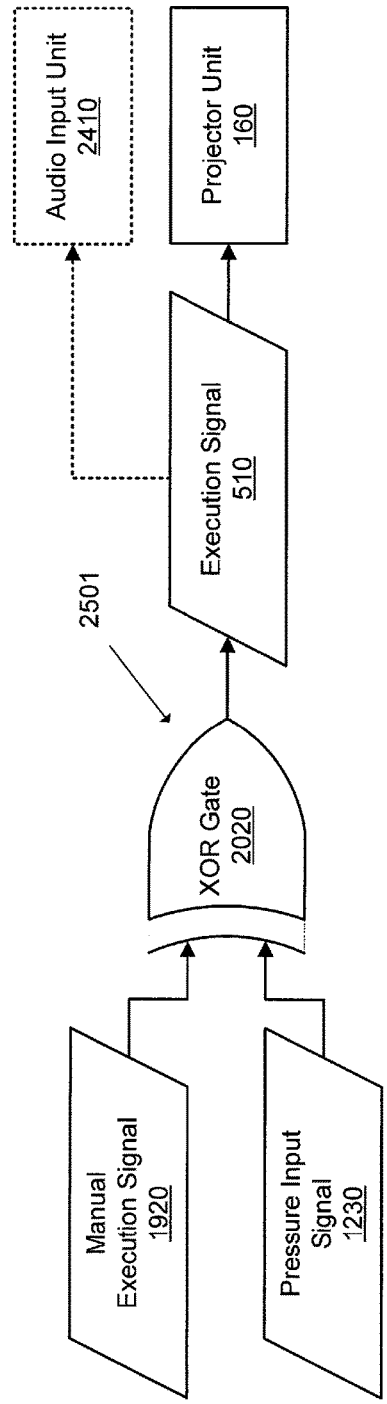
FIG. 25A
FIG. 25B

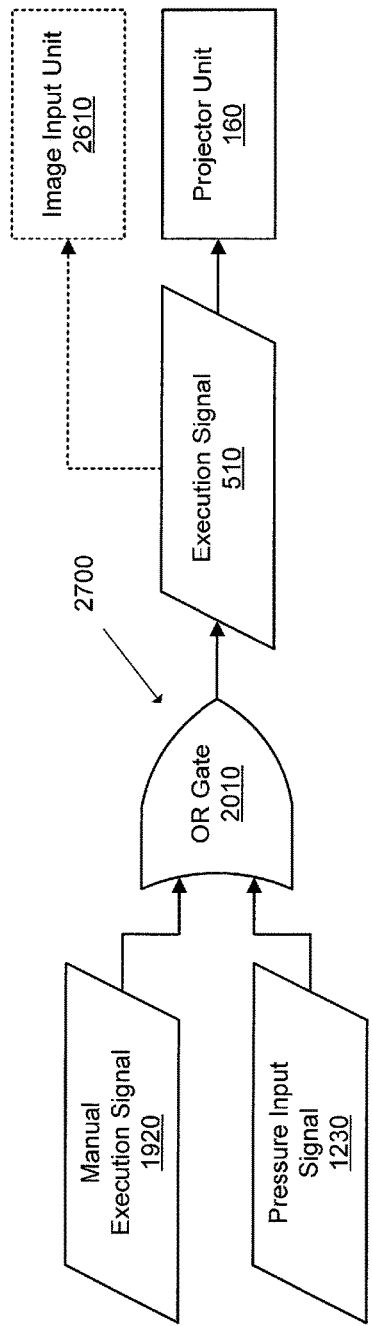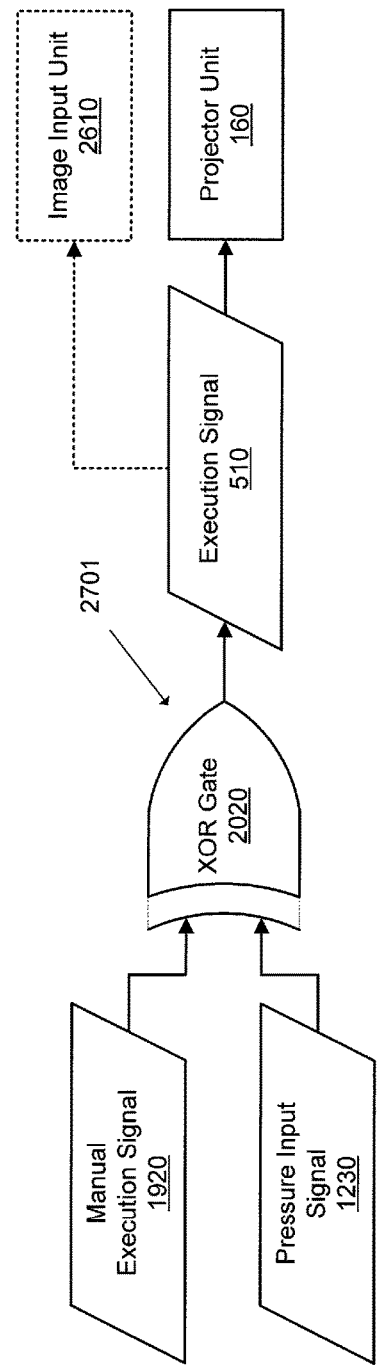

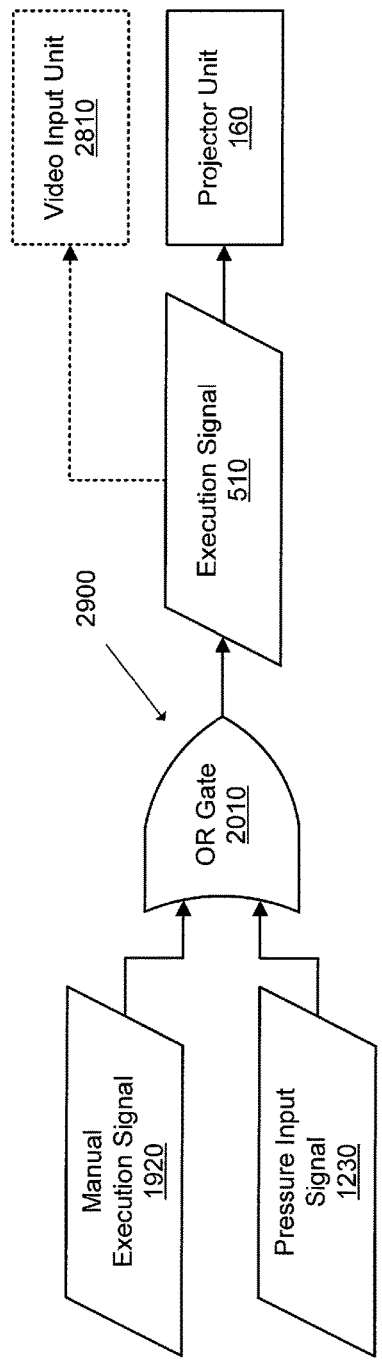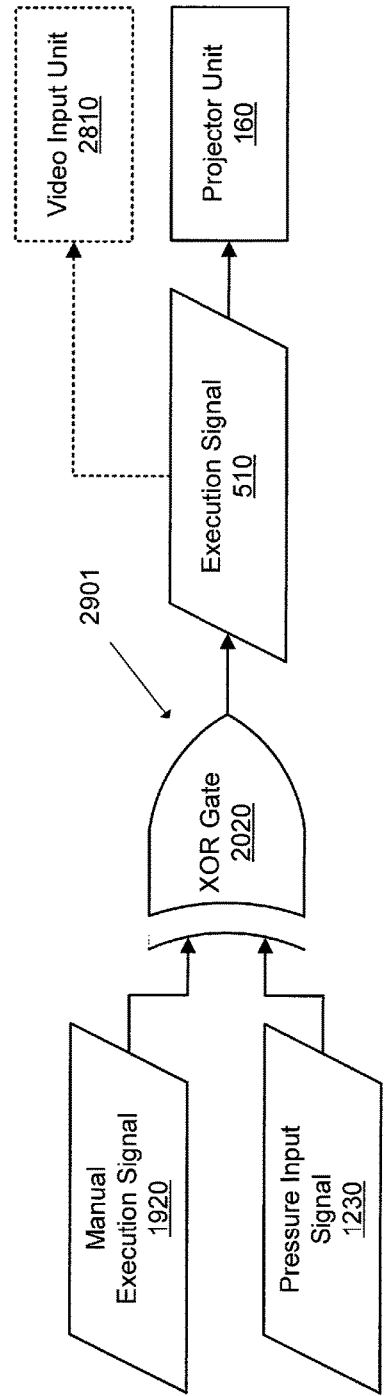
FIG. 29A
FIG. 29B

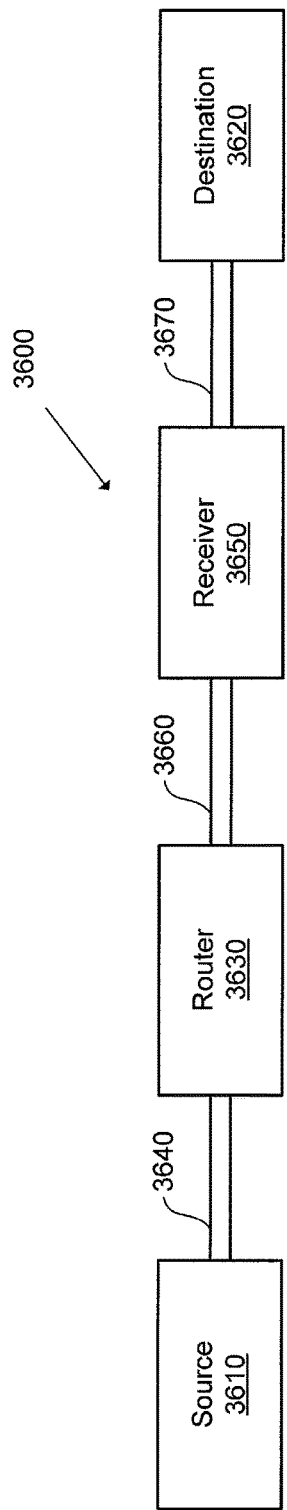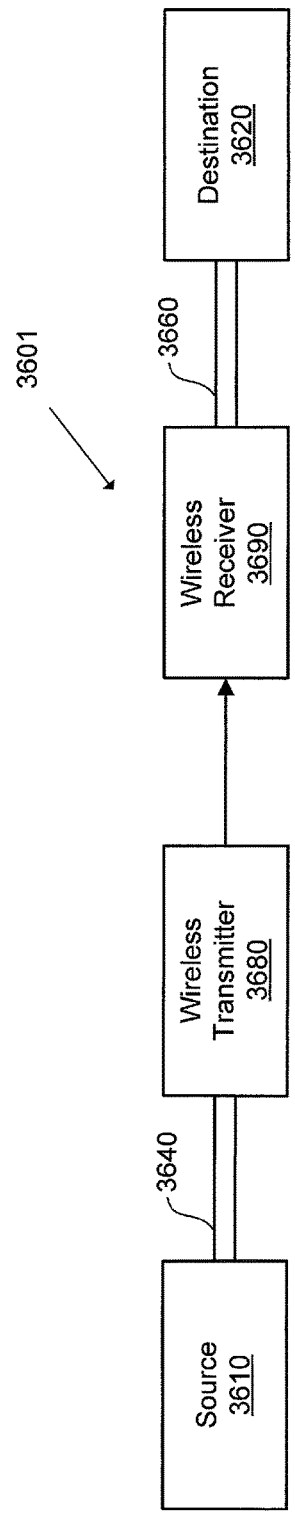
FIG. 36A
FIG. 36B

SELF-DEFENSE SYSTEM

CROSS REFERENCE TO RELATED APPLICATIONS

This application is a Divisional of U.S. patent application Ser. No. 14/280,542, filed on May 16, 2014, which claims the benefit of U.S. patent application Ser. No. 13/181,467, filed on Jul. 12, 2011. This application hereby claims the benefit of and priority to U.S. patent application Ser. No. 13/181,467 and U.S. patent application Ser. No. 14/280,542, each of which is hereby incorporated by reference in its entirety.

TECHNICAL FIELD

The present application relates to the field of self-defense systems.

BACKGROUND

The concept of self-defense can oftentimes be more important to a person's life than his or her financial livelihood. Whereas lost income or possessions can be replaced in time, physical damage to one's life and limb may be irreparable. As such, self-defense systems and devices can play an important role in many modern scenarios that present obstacles to self-preservation. Indeed, many of these systems and devices may be implemented to ward off attackers, and may be utilized by law enforcement officers as well as civilian populations for purposes of crime prevention and the overall protection of life and limb.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

In an embodiment, a self-defense system is disclosed. The self-defense system may include or comprise a material sized to conform to an appendage, and a defense unit coupled with the material and positioned to initiate a defense event in response to an input.

Additionally, in an embodiment, a self-defense system is disclosed, wherein the self-defense system may include or comprise a material sized to conform to an appendage, and first and second projector units coupled with the material and positioned to project one or more substances in first and second directions, respectively.

Moreover, in an embodiment, a self-defense system is disclosed, wherein the self-defense system may include or comprise a material sized to conform to an appendage, and a projector unit coupled with the material at a coupling surface area and positioned to project a substance in a direction that is substantially normal to the coupling surface area and/or substantially perpendicular to an axis corresponding to a longest length of the appendage.

Furthermore, in an embodiment, a self-defense system is disclosed, wherein the self-defense system may include or comprise a material sized to conform to an appendage, a comparator configured to conduct a comparison of two electronic signals and generate an automatic execution signal based on the comparison, and a defense unit associated with the comparator and coupled with the material, wherein the defense unit is positioned to initiate a defense event based on the automatic execution signal.

Additionally, in an embodiment, a self-defense system is disclosed, wherein the self-defense system may include or comprise a material sized to conform to an appendage, a pressure sensor unit positioned to sense an applied pressure and generate a pressure input signal based on the applied pressure, and a defense unit associated with the pressure sensor unit and coupled with the material, the defense unit positioned to initiate a defense event based on the pressure input signal.

Moreover, in an embodiment, a self-defense system is disclosed, wherein the self-defense system may include or comprise a material sized to conform to an appendage, and a defense unit coupled with the material. The defense unit may include or comprise a nozzle sized to engage a container configured to contain a substance under pressure, and an appendage anchor sized to receive a first digit so as to anchor a second digit relative to the nozzle and enable the second digit to manually push the container toward the nozzle.

DESCRIPTION OF THE DRAWINGS

The accompanying drawings, which are incorporated in and form a part of this specification, illustrate embodiments of the present technology, and, together with the Detailed Description, serve to explain principles discussed below.

FIG. 2 is a diagram of a third exemplary self-defense system in accordance with an embodiment.

FIG. 19 is a diagram of a tenth exemplary self-defense system in accordance with an embodiment.

FIG. 20A is a diagram of a first exemplary logic system in accordance with an embodiment.

FIG. 20B is a diagram of a second exemplary logic system in accordance with an embodiment.

FIG. 25A is a diagram of a fifth exemplary logic system in accordance with an embodiment.

FIG. 25B is a diagram of a sixth exemplary logic system in accordance with an embodiment.

FIG. 27A is a diagram of a seventh exemplary logic system in accordance with an embodiment.

FIG. 27B is a diagram of an eighth exemplary logic system in accordance with an embodiment.

FIG. 29A is a diagram of a ninth exemplary logic system in accordance with an embodiment.

FIG. 29B is a diagram of a tenth exemplary logic system in accordance with an embodiment.

FIG. 36A is a diagram of a first exemplary communication arrangement in accordance with an embodiment.

FIG. 36B is a diagram of a second exemplary communication arrangement in accordance with an embodiment.

Figure 1A:
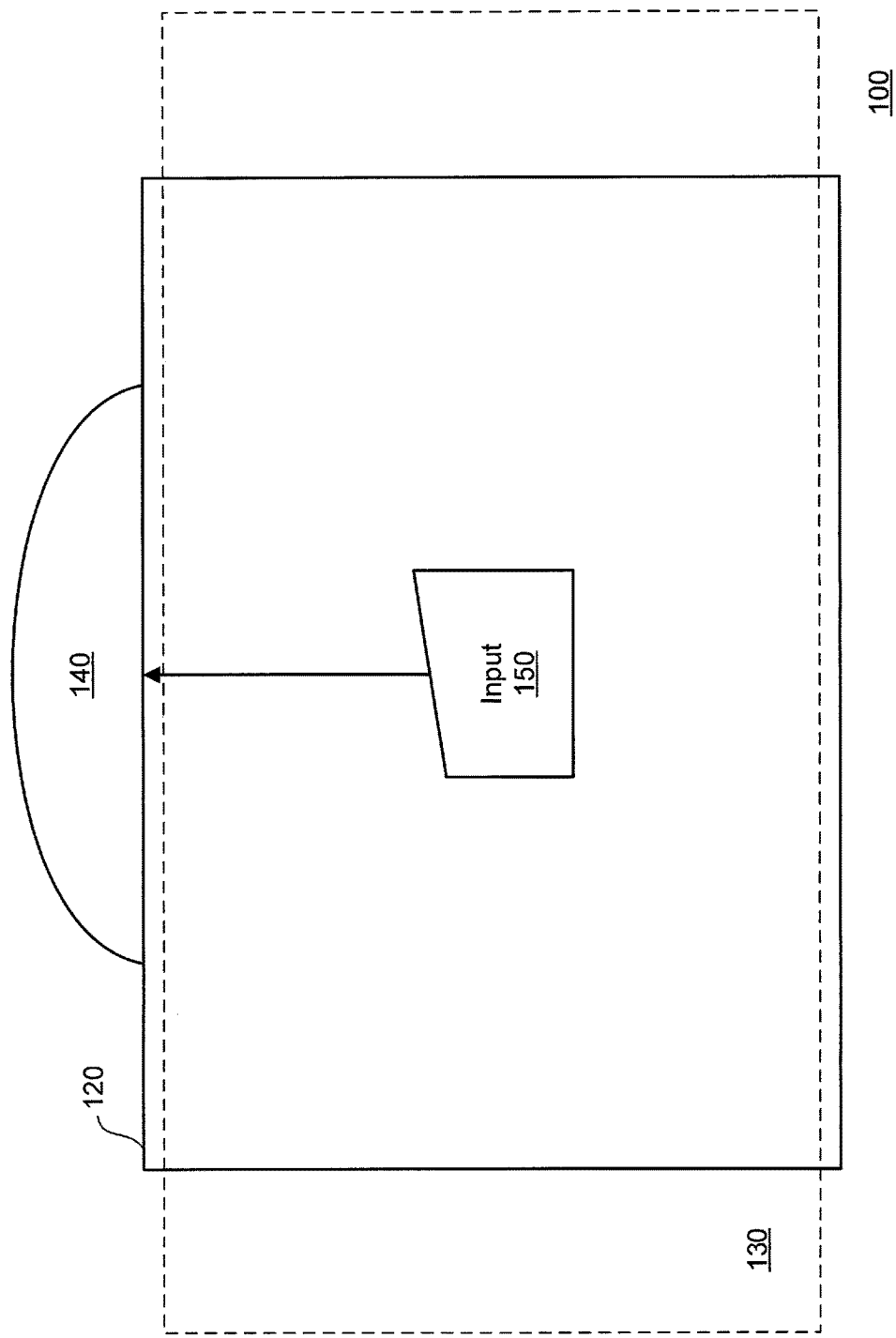
FIG. 1A is a diagram of a first exemplary self-defense system in accordance with an embodiment.

The drawings referred to in this description are not to be understood as being drawn to scale except if specifically noted, and such drawings are only exemplary in nature.

DETAILED DESCRIPTION

Reference will now be made in detail to embodiments of the present technology, examples of which are illustrated in the accompanying drawings. While the present technology will be described in conjunction with various embodiments, these embodiments are not intended to limit the present technology. Rather, the present technology is to be understood as encompassing various alternatives, modifications and equivalents.

Additionally, in the following Detailed Description, numerous specific details are set forth in order to provide a thorough understanding of the present technology. However, the present technology may be practiced without these specific details. In other instances, well-known methods, procedures, components, and circuits have not been described in detail so as to not unnecessarily obscure aspects of the exemplary embodiments presented herein.

Moreover, it is noted that discussions throughout the present detailed description that utilize terms indicating that some action or process is to occur may refer to the actions and processes of a computer system, or a similar electronic computing device. For example, the computer system or similar electronic computing device manipulates and transforms data represented as physical (e.g., electronic) quantities within the computer system's registers and memories into other data similarly represented as physical quantities within the computer system memories or registers, or other such information storage, transmission, or display devices. The present technology is also well-suited to the use of other computer systems, such as, for example, optical and mechanical computers.

The foregoing notwithstanding, it is further noted that terms indicating that some action or process is to occur may refer to manual actions or processes. Indeed, various embodiments of the present technology implement a combination of one or more computer-implemented actions or processes with one or more manual actions or processes.

Furthermore, for purposes of clarity, the term "appendage" may be construed as being, for example, an arm, hand, finger, thumb, leg, foot, toe, or any other physical appendage. Additionally, the term "digit" may be construed as being, for example, a finger, thumb or toe, although the term digit is not to be limited to such constructions. Moreover, the term "substance" may be construed as referring to, for example, a gaseous, liquid, plasma or solid substance, or any combination thereof.

Furthermore, the terminology "coupled with" shall not be construed as intending a direct physical relationship. For example, when two components are described as being "coupled with" one another, there may be one or more other parts, materials, etc. (e.g., an adhesive or a signal/transmission line), that are coupled between, attaching, integrating, etc., the two components. As such, the terminology "coupled with" shall be given its broadest meaning, unless otherwise indicated.

Overview

Pursuant to an exemplary scenario, a person, such as a jogger, notices a dog running toward him in a menacing manner, as if the dog intends to attack. Upon seeing this, the person immediately raises his arms in front of his face in a natural, defensive posture due to an innate defensive reflex prompted by fear and adrenaline. The person's arms are now positioned between his face and torso and the attacking dog such that the person's vital organs are provided a degree of protection. When the dog reaches the person, the dog bites down on one of the person's arms, which are closer in proximity to the dog than the person's face and torso. The dog then pulls and tears at the person's arm, thus inflicting a significant degree of damage to the bitten limb.

In one example, this problem is remedied when the user carries a pepper spray propulsion device. However, in so much as the user must extend his arm toward the attacking dog when discharging the chemical agent, the user has consequently sacrificed his defensive posture and exposed his vital organs to harm. If the user fails to spray the dog with the chemical agent in a manner that stops the attack, then the dog may latch on to the user's face or torso, thereby causing the user to suffer even more harm than in the previous example (whereby the user's natural, defensive posture was not sacrificed). Furthermore, the user may not even have time to aim the device if the attack happens suddenly and the device is, for example, in the user's pocket.

In an embodiment of the present technology, a self-defense system is provided that makes use of a person's natural, defensive posture when initiating a defense event. Consider the example where an implemented self-defense system includes a piece of material that wraps around a person's arm or hand such that the self-defense system may be comfortably worn when the user is jogging. The self-defense system also includes a chemical projector unit, such as a pepper spray propulsion device, positioned so as to be aimed at an oncoming attacker automatically when the user raises his arms in front of his face in a natural, defensive posture during the attack. In this manner, the attacker can be sprayed with a defensive chemical agent without the user sacrificing his natural, defensive posture, which is in stark contrast to the aforementioned pepper spray propulsion device that requires the user to extend his arm toward the oncoming attacker when discharging the chemical agent, which consequently sacrifices the user's defensive posture and exposes the user's vital organs to harm.

Furthermore, in so much as the device is worn on the user's arm, the user does not need to spend precious seconds during an attack removing the device from his pocket, nor does the user need to constantly carry the device in his hand when he is not being attacked. Rather, an embodiment provides that the device is comfortably worn on the user's arm, or on the back of the user's hand (e.g., opposite the palm region), such that the user's hands are free to engage in other activities, all while the device is constantly available to be implemented at a moment's notice when the user adopts the aforementioned natural, defensive posture.

It is noted that the foregoing examples are provided for purposes of illustration, and that the present technology may also be implemented in a similar manner, both by law enforcement officers and civilian citizens, to fend off human attackers. Indeed, the present technology has a significant degree of utility for law enforcement officers, who must have their hands free to activate their primary weapons (e.g., their service firearms). In so much as a number of the self-defense devices discussed herein may be comfortably mounted on the officers' arms, these devices may function as effective back-up defense systems in close-quarter combat situations if the officers' primary weapons are lost, malfunction, or are otherwise inoperable or ineffective.

Various exemplary embodiments of the present technology will now be discussed. It is noted, however, that the present technology is not limited to these exemplary embodiments, and that the present technology also includes obvious variations of the exemplary embodiments and implementations described herein. It is further noted that various well-known components are generally not illustrated in the drawings so as to not unnecessarily obscure various principles discussed herein, but that such well-known components may be implemented by those skilled in the art to practice various embodiments of the present technology.

Exemplary Systems and Configurations

With reference now to FIG. 1A, a first exemplary self-defense system 100 in accordance with an embodiment is shown. First exemplary self-defense system 100 includes or comprises a material 120 sized to conform to an appendage 130, such as a user's hand, wrist or lower arm. In one embodiment, material 120 includes or comprises a physical material selected from a group of materials consisting essentially of leather, cloth, rubber and neoprene. It is noted, however, that other materials may be implemented.

It is further noted that material 120 may include or comprise a number of components that are each elastic or inelastic such that material 120 is able to conform to a shape of appendage 130. Indeed, one exemplary implementation provides that a portion of material 120 includes or comprises a hand, wrist or lower arm unit sized to conform to a user's hand, wrist or lower arm such that the user may quickly position material 120 between the user's face or torso and an oncoming threat simply by repositioning the user's hand, wrist or lower arm, such as when the user adopts a defensive posture. The foregoing notwithstanding, one embodiment provides that material 120 is an optional component.

With reference still to FIG. 1A, first exemplary self-defense system 100 includes or comprises a defense unit 140 coupled or associated with material 120 and positioned to initiate a defense event in response to an input 150. Such a defense event may include, for example, (1) spraying a substance (e.g., a lachrymatory agent or pepper spray), (2) generating a voltage differential across two electrodes of a stun gun, (3) projecting a projectile (e.g., a rubber bullet), (4) sounding an alarm, (5) capturing information pertaining to the event, and/or (6) routing an amount of captured information to a preselected entity (e.g., a law enforcement agency). However, other defense events may also be implemented.

In an embodiment, input 150 is a manual input, such as when a user pushes a button to initiate a defense event, or such as when a user manually pushes a pressurized container toward a release nozzle, or vice versa. Pursuant to one embodiment, however, input 150 is an electronic or optical signal configured to cause defense unit 140 to initiate a defense event. Indeed, it is noted that input 150 is not to be limited to any particular type of input, and that various types of inputs may be implemented.

Figure 1B:
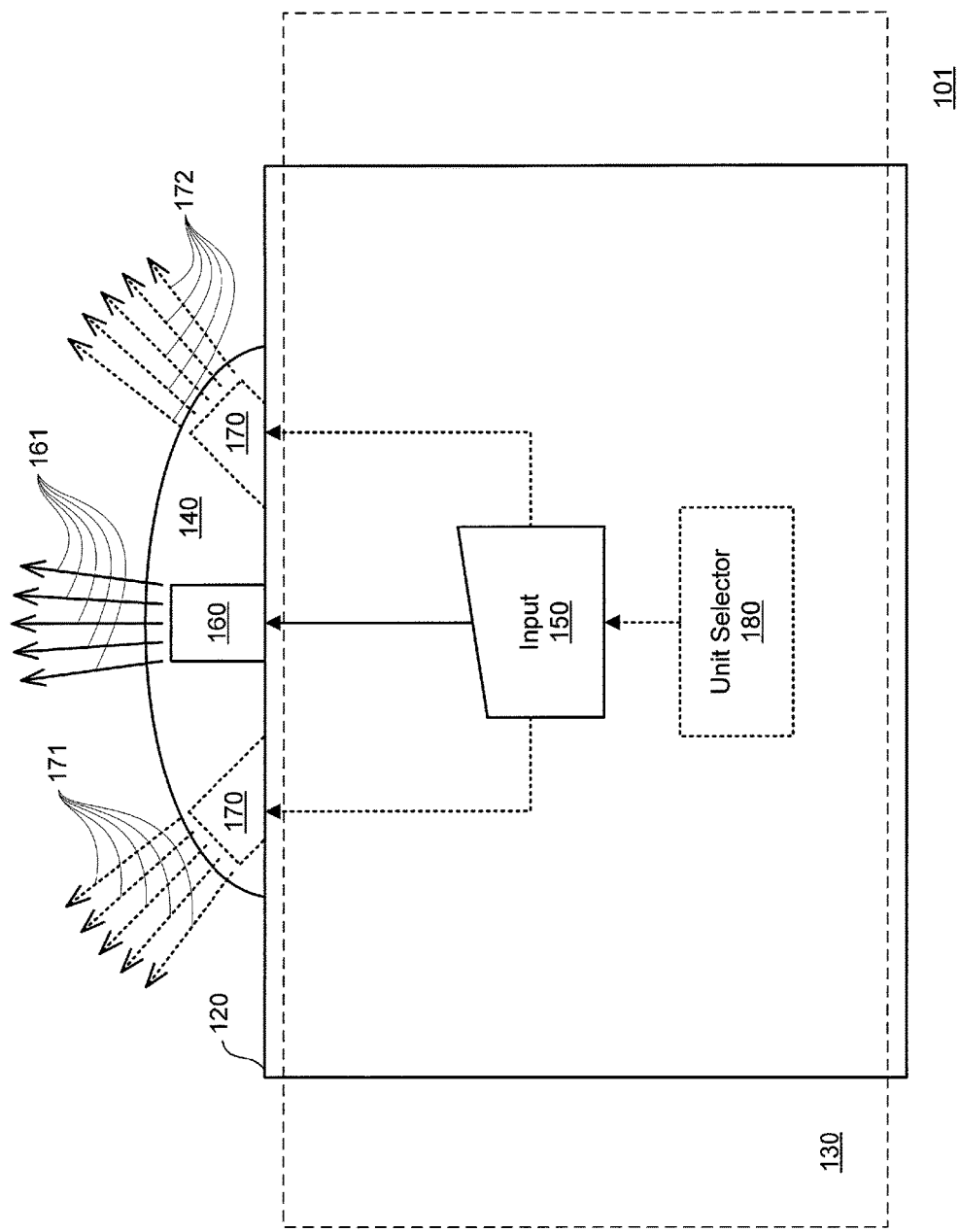
FIG. 1B is a diagram of a second exemplary self-defense system in accordance with an embodiment.

With reference now to FIG. 1B, a second exemplary self-defense system 101 in accordance with an embodiment is shown. Second exemplary self-defense system 101 includes or comprises a projector unit 160 coupled or associated with defense unit 140 and positioned to project a substance in one or more of exemplary directions 161. Second exemplary self-defense system 101 may also optionally include or comprise one or more additional projector units 170 coupled or associated with material 120 and positioned to project one or more substances in a number of different directions, respectively, such as in exemplary directions 171, 172. In this manner, more than one projector unit may be implemented to increase the lateral range in which a substance is projected.

Moreover, one embodiment provides that input 150 is configured to communicate to defense unit 140 which of the implemented projector units are to be utilized during a specific defense event. To illustrate, and with reference still to FIG. 1B, a unit selector 180 may be optionally implemented to enable a user to manually select how many of the implemented projector units are to spray a chemical agent during a defense event. In this manner, input 150 may be utilized to increase or decrease the lateral range in which a substance is projected by either increasing or decreasing the selected number of projector units.

Additionally, it is noted that the various projector units may be configured to project different substances, respectively, wherein each of these substances is housed in a different container. In one embodiment, however, the various projector units may be configured to project the same substance (e.g., a lachrymatory agent or pepper spray) from the same or different containers. For example, a single pressurized container may be implemented with multiple nozzles, or with a single nozzle having multiple chambers defined therein, such that the substance under pressure is provided multiple paths from which to leave the container during a defense event. In this manner, more than one projector unit will be implemented, although a single container is provided.

Moreover, and with reference still to FIG. 1B, an embodiment provides that input 150 is routed to each of projector unit 160 and one or more additional projector units 170. However, other event initiation paradigms may be implemented, such as where input 150 is routed to defense unit 140, whereby defense unit 140 then proactively initiates the various projection units. For example, defense unit 140 may be integrated with a controller unit configured to activate one or more projector units associated with defense unit 140 in response to sensing or receiving input 150.

Furthermore, although second exemplary self-defense system 101 is described as comprising or including a number of projection units, an embodiment provides a self-defense system including, comprising or integrated with a number of other types of self-defense units, such as conductive energy devices (e.g., stun guns), instead of or in addition to the projection units. A number of exemplary defense devices are discussed below with reference to FIG. 3.

With reference now to FIG. 2, a third exemplary self-defense system 200 in accordance with an embodiment is shown. Third exemplary self-defense system 200 includes or comprises an armor unit 210 coupled or associated with material 120, wherein armor unit 210 has a degree of rigidity such that armor unit 210 is able to prevent a degree of damage from occurring to appendage 130 when a force is applied to material 120 in a direction toward appendage 130.

Consider the example where a user is attacked by a dog when material 120 is wrapped around the user's arm. In response to the user raising his or her arm between the user and the attacking dog, which is a natural human defense impulse during an attack situation, material 120 and armor unit 210 is displaced between the dog and the user's face and torso. The dog then bites down on material 120 and armor unit 210, which is closer to the dog than the user's face and torso. As a result of armor unit 210, the user's bitten arm suffers less damage than it would have if no armor had been implemented.

With reference still to FIG. 2, third exemplary self-defense system 200 may also include or comprise a number of additional armor units 220 coupled or associated with material 120. In an embodiment, the various armor units are sized to conform to a shape of appendage 130, such as to minimize a degree of comfort associated with material 120. Additionally, the armor units may be formed from a physical material selected from a group of materials consisting essentially of, for example, plastic, metal alloys and synthetic fibers, such as para-aramid synthetic fibers (e.g., poly para-phenyleneterephthalamide). It is noted, however, that other materials may be implemented.

Figure 3B:
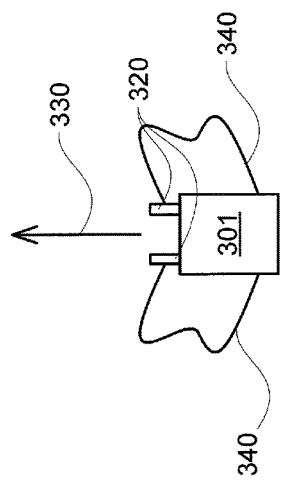
FIG. 3B is a diagram of an exemplary conductive energy device in accordance with an embodiment.
Figure 3C:
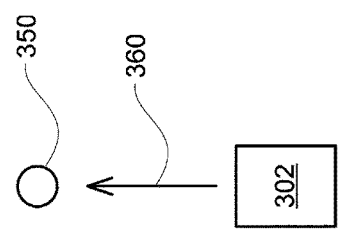
FIG. 3C is a diagram of a second exemplary projector unit in accordance with an embodiment.
Figure 3A:
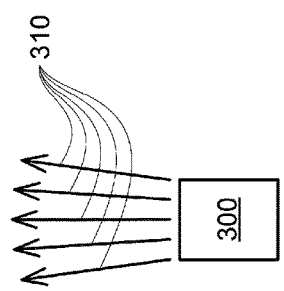
FIG. 3A is a diagram of a first exemplary projector unit in accordance with an embodiment.

With reference now to FIG. 3A, a first exemplary projector unit 300 in accordance with an embodiment is shown. First exemplary projector unit 300 is configured to project a substance, such as a chemical substance (e.g., a lachrymatory agent or pepper spray), in a number of projection directions 310 in response to an input. Consider the example where first exemplary projector unit 300 is integrated with a nozzle sized to engage a pressurized container housing a chemical substance. In response to a distance between the nozzle and the container decreasing below a preselected distance threshold, the chemical substance is forced out of the container and through a chamber formed in the nozzle. The substance then exits the nozzle in multiple different directions that define a dispersed spray area rather than in a single direction.

With reference now to FIG. 3B, an exemplary conductive energy device 301 in accordance with an embodiment is shown. Exemplary conductive energy device 301 includes or comprises two electrodes 320, and is configured to generate a voltage differential between electrodes 320, wherein, this voltage differential is high enough to disable an attacker with an electric shock or current. Indeed, in accordance with an embodiment, the generated voltage differential is above 50 kilovolts (kV) such that an attacker is momentarily stunned or disabled when coming into contact with electrodes 320.

In one embodiment, exemplary conductive energy device 301 is configured to propel electrodes 320 in a propulsion direction 330 so as to increase an effective range of the device. In particular, electrodes 320 are propelled, such as by compressed gas (e.g., nitrogen) charges, and continue to remain connected to exemplary conductive energy device 301 by conductive wires 340. Once electrodes 320 come into contact with an attacker, an electric current is delivered through conductive wires 340 and electrodes 320 so as to disrupt voluntary control of the attacker's muscles to thereby end the attack in a non-lethal manner.

With reference now to FIG. 3C, a second exemplary projector unit 302 in accordance with an embodiment is shown. Second exemplary projector unit 302 is configured to project a projectile 350, such as a non-lethal rubber bullet, in a projection direction 360, such as by compressed gas or combustible powder charges. In accordance with an exemplary implementation, projectile 350 is projected with enough force to temporarily incapacitate an attacker so as to enable a safe retreat from the attack.

The foregoing notwithstanding, it is noted that the present technology is not limited to the exemplary defense devices discussed herein. Indeed, other types of defense devices may be implemented.

Figure 4:
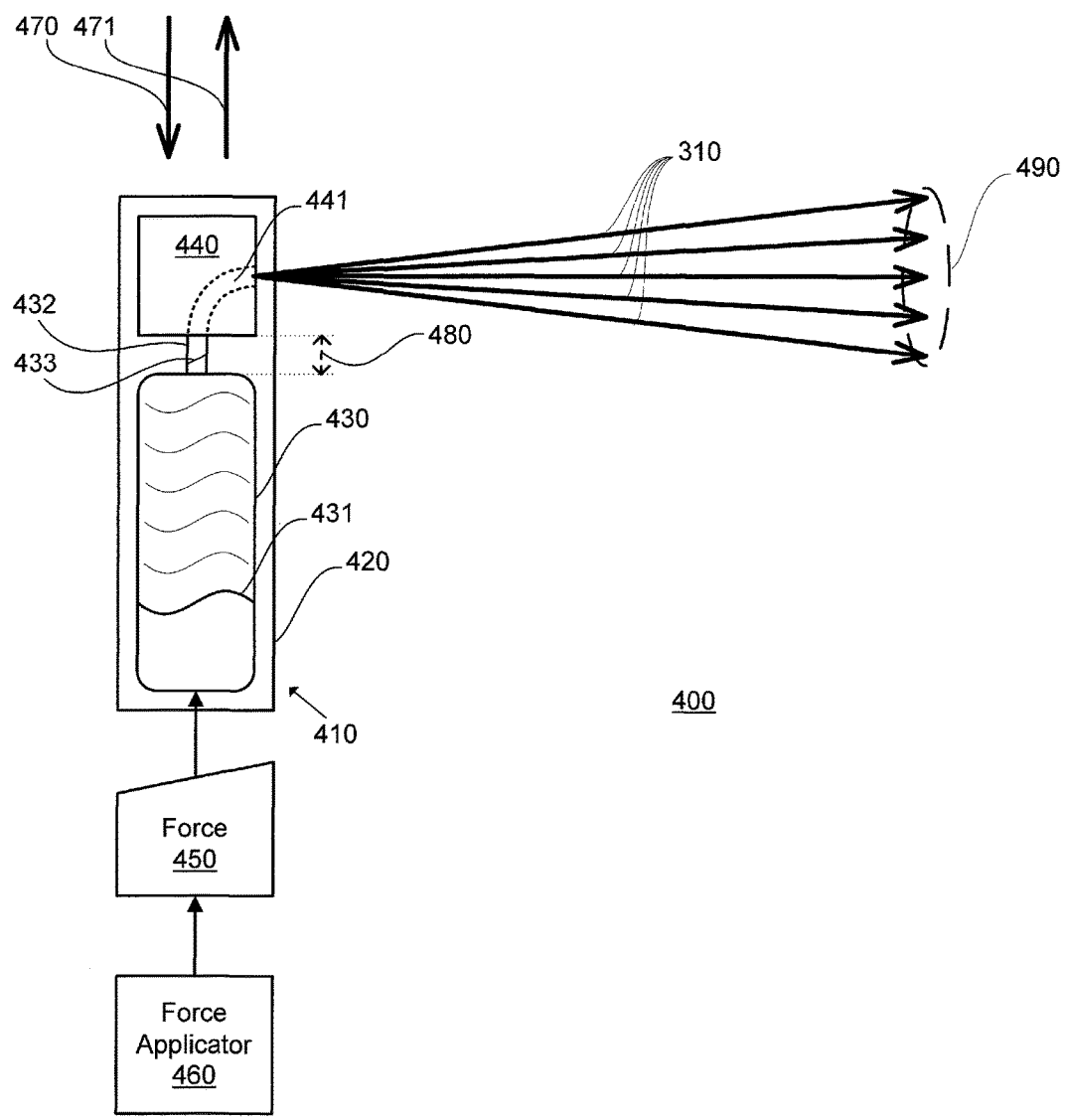
FIG. 4 is a diagram of an exemplary projection configuration in accordance with an embodiment.
Figure 5:
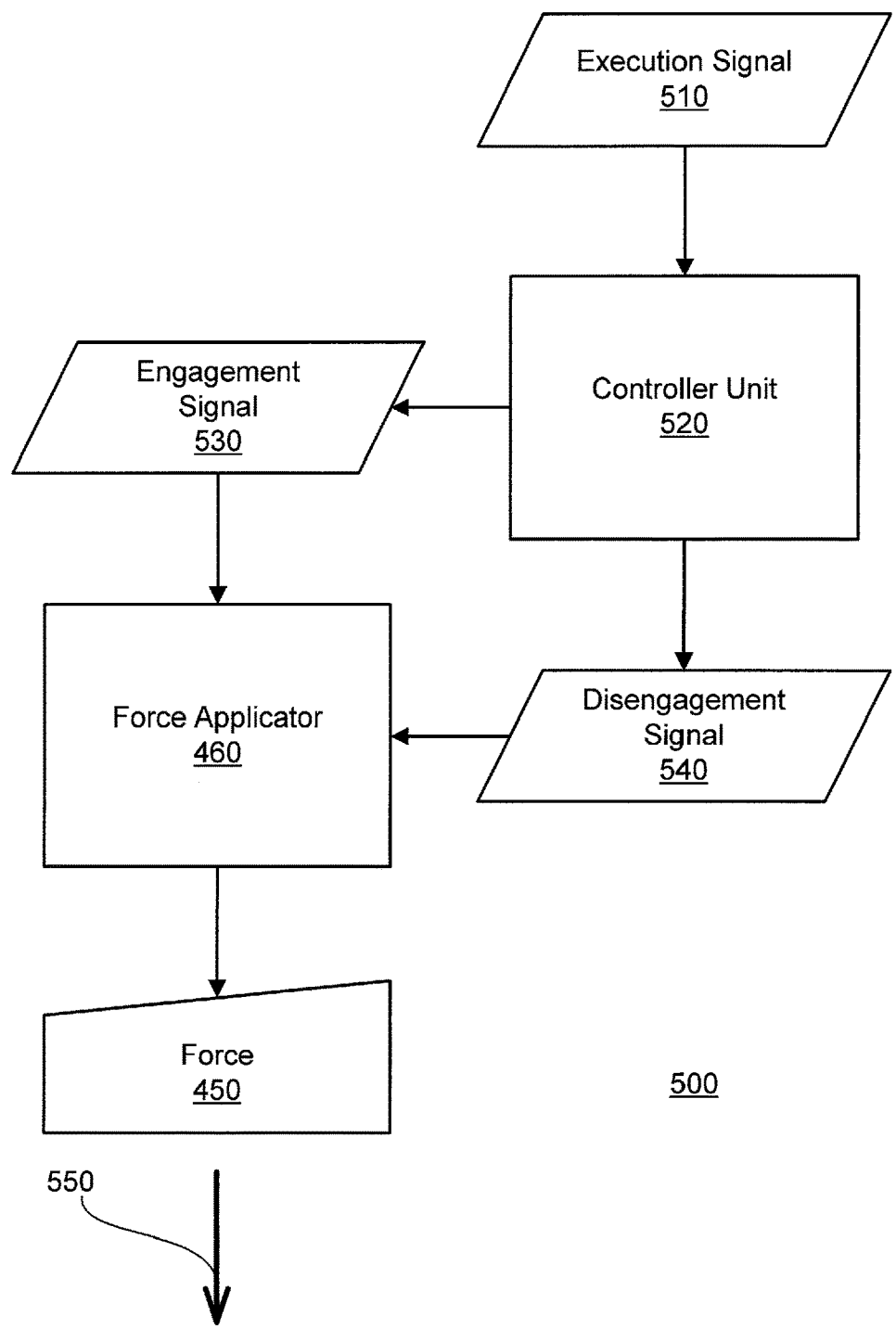
FIG. 5 is a diagram of a first exemplary engagement configuration in accordance with an embodiment.

With reference now to FIG. 4, an exemplary projection configuration 400 in accordance with an embodiment is shown. A projection unit 410, such as first exemplary projector unit 300 shown in FIG. 3A, includes or comprises a housing 420 sized to house a container 430, wherein container 430 is configured to contain a substance 431 under pressure, such as a chemical substance (e.g., a lachrymatory agent or pepper spray). Housing 420 may also house a nozzle 440 sized to engage container 430 and release an amount of substance 431 from container 430 in response to a force 450 being applied to nozzle 440 or container 430, such as by a force applicator 460, in a preselected direction and above a preselected magnitude.

Consider the example where container 430 includes, comprises or is integrated with a valve stem 432. A chamber 441 is formed or defined within nozzle 440, wherein chamber 441 is sized to engage or receive valve stem 432. When force applicator 460 pushes nozzle 440 in a first direction 470 toward container 430, or when force applicator 460 pushes container 430 in a second direction 471 toward nozzle 440, such that a distance 480 between container 430 and nozzle 440 decreases, a pressure valve 433 coupled with or formed within valve stem 432 opens to release an amount of substance 431 from container 430. In so much as the internal pressure of container 430 is above atmospheric pressure, the released amount of substance 431 is forced through valve stem 432 and chamber 441 and finally projected from nozzle 440 in projection directions 310, which define a dispersed spray area 490. It is noted that dispersing a chemical agent across a dispersed spray area may increase the effectiveness of an initiated defense event, such as by increasing the probability that the chemical agent will come into contact with an attacker's eyes, nose and mouth.

With reference now to FIG. 5, a first exemplary engagement configuration 500 in accordance with an embodiment is shown. In particular, an execution signal 510 is routed to a controller unit 520, wherein controller unit 520 is configured to generate engagement and disengagement signals 530, 540 based on execution signal 510. Engagement and disengagement signals 530, 540 are routed to force applicator 460, wherein force applicator 460 then increases or decreases force 450, which is directed in preselected force engagement direction 550, based on these signals.

To illustrate, and with reference again to FIG. 4, consider the example where execution signal 510 communicates to controller unit 520 that a defense event is to be initiated, and, consequently, controller unit 520 generates engagement signal 530 which is routed to force applicator 460. It is noted that force applicator 460 is positioned to apply force 450 to nozzle 440 or container 430 in a preselected direction and above a preselected magnitude in response to engagement signal 530 such that a first amount of substance 431 is released from container 430. However, when execution signal 510 is halted, or otherwise communicates to controller unit 520 that a defense event is to be paused or ended, controller unit 520 generates disengagement signal 540, which is routed to force applicator 460. Force applicator 460 is configured to decrease a magnitude of force 450 below the preselected magnitude in response to disengagement signal 540 such that a release of a second amount of substance 431 from container 430 is prevented. In this manner, controller unit 520 may be implemented to both initiate and end a defense event.

It is noted that the present technology is not limited to any particular type of force applicator. For example, force applicator 460 may include or comprise a linear stepper motor configured to generate an amount of linear force based on execution signal 510. Pursuant to one embodiment, however, force applicator 460 includes or comprises a component, such as a miniature camshaft lobe, configured to translate rotational force into linear force. The foregoing notwithstanding, it is noted that other types of force applicators may be implemented.

With reference still to FIG. 5, controller unit 520 is configured to generate engagement and disengagement signals 530, 540 based on execution signal 510. In one embodiment, execution signal 510 is based on one or more signals discussed herein, such as a pressure input or manual execution signal as discussed infra. In this manner, execution signal 510 may be generated based on a sensed input (e.g., an applied pressure or a manual user selection) such that a defense event is automatically initiated or terminated based on the sensed input.

With reference now to FIG. 6, a second exemplary engagement configuration 600 in accordance with an embodiment is shown. Second exemplary engagement configuration 600 is similar to first exemplary engagement configuration 500, except that engagement and disengagement signals 530, 540 are routed from controller unit 520 to a voltage generator 610, wherein voltage generator 610 is associated or coupled with exemplary conductive energy device 301. Voltage generator 610 generates a voltage differential 620 based on engagement and disengagement signals 530, 540, and voltage differential 620 is applied across electrodes 320, such as by applying voltage differential 620 to conductive wires 340.

To illustrate, consider the example where execution signal 510 communicates to controller unit 520 that a defense event is to be initiated, and, consequently, controller unit 520 generates engagement signal 530, which is routed to voltage generator 610. In response to receiving engagement signal 530, voltage generator 610 generates voltage differential 620 such that voltage differential 620 is at or above a predetermined voltage threshold (e.g., 50 kV), and voltage differential 620 is applied across electrodes 320. However, when execution signal 510 is halted, or otherwise communicates to controller unit 520 that a defense event is to be paused or ended, controller unit 520 generates disengagement signal 540, which is routed to voltage generator 610. Consequently, voltage generator 610 ceases to continue to generate voltage differential 620 and/or decreases the previously generated voltage differential 620 below the aforementioned voltage threshold.

With reference now to FIG. 7, a third exemplary engagement configuration 700 in accordance with an embodiment is shown. Third exemplary engagement configuration 700 is similar to first exemplary engagement configuration 500, except that engagement and disengagement signals 530, 540 are routed from controller unit 520 to a signal generator 710. Signal generator 710 generates a projection signal 720 based on engagement and disengagement signals 530, 540, and projection signal 720 is routed to a projector 730, which is provided with an amount of projectiles 740. Projector 730 is configured to project a projectile 350 (e.g., a non-lethal rubber bullet) from among the amount of projectiles 740, based on projection signal 720, in a projection direction 360, such as by compressed gas or combustible powder charges.

To illustrate, consider the example where execution signal 510 communicates to controller unit 520 that a defense event is to be initiated, and, consequently, controller unit 520 generates engagement signal 530, which is routed to signal generator 710. In response to receiving engagement signal 530, signal generator 710 generates projection signal 720, which communicates to projector 730 that one or more projectiles from among projectiles 740 are to be projected in projection direction 360. However, when execution signal 510 is halted, or otherwise communicates to controller unit 520 that a defense event is to be paused or ended, controller unit 520 generates disengagement signal 540, which is routed to signal generator 710. Consequently, signal generator 710 halts projection signal 720, or otherwise configures projection signal 720 to communicate to projector 730 that the projection of projectiles by projector 730 is to be paused or ended.

It is noted that first, second and third exemplary engagement configurations 500, 600, 700 may be implemented in conjunction with first exemplary projector unit 300, exemplary conductive energy device 301, and second exemplary projector unit 302, respectively (see FIGS. 3A-3C). It is further noted, however, that the present technology is not limited to these exemplary engagement configurations. Indeed, other engagement configurations may be implemented.

Figure 8A:
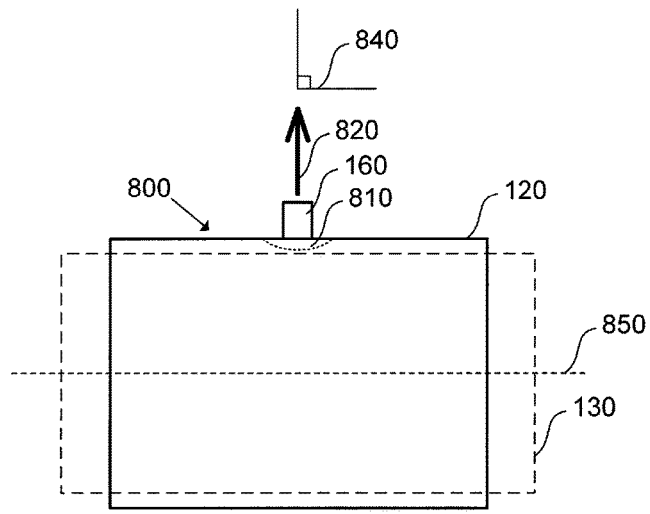
FIGS. 8A-8C are diagrams of a first exemplary defense arrangement in accordance with an embodiment.
Figure 8B:
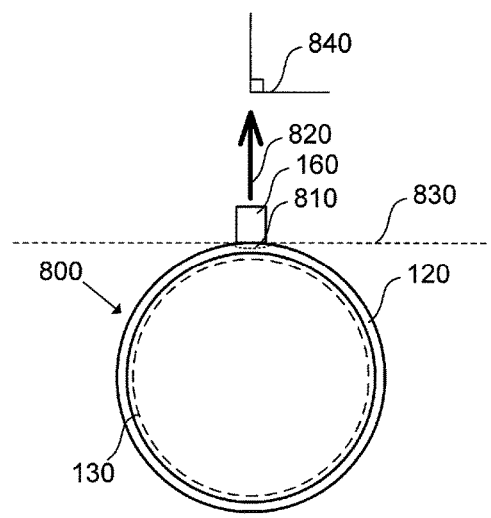
Figure 8C:
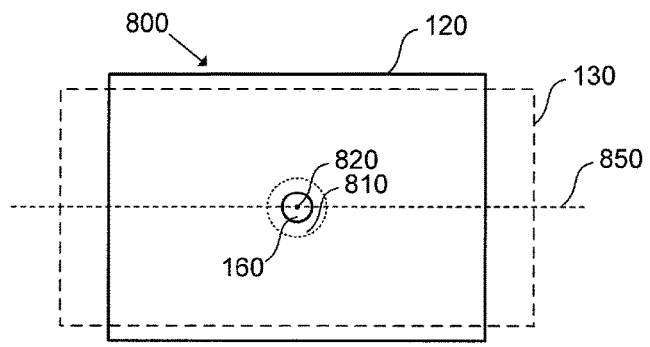

With reference now to FIGS. 8A-8C, a first exemplary defense arrangement 800 in accordance with an embodiment is shown. In particular, a defense device, such as projector unit 160, is coupled with material 120 at a coupling surface area 810 and positioned to project a substance in a direction 820 that is substantially normal to coupling surface area 810 (as represented by surface axis 830 and right angle 840) and/or substantially perpendicular to an axis corresponding to a longest length of appendage 130 (as represented by major length axis 850 and right angle 840). Pursuant to one embodiment, however, direction 820 is angled approximately 45 degrees or more (e.g., approximately 60 degrees) away from major length axis 850. It is noted that such an arrangement may increase an effectiveness of a defense event, such as when users naturally position their arms in front of their faces in a defensive posture such that projecting a substance in such a direction causes the substance to be projected toward the oncoming attacker without necessitating a change in the natural, defensive posture of the users.

Figure 9:
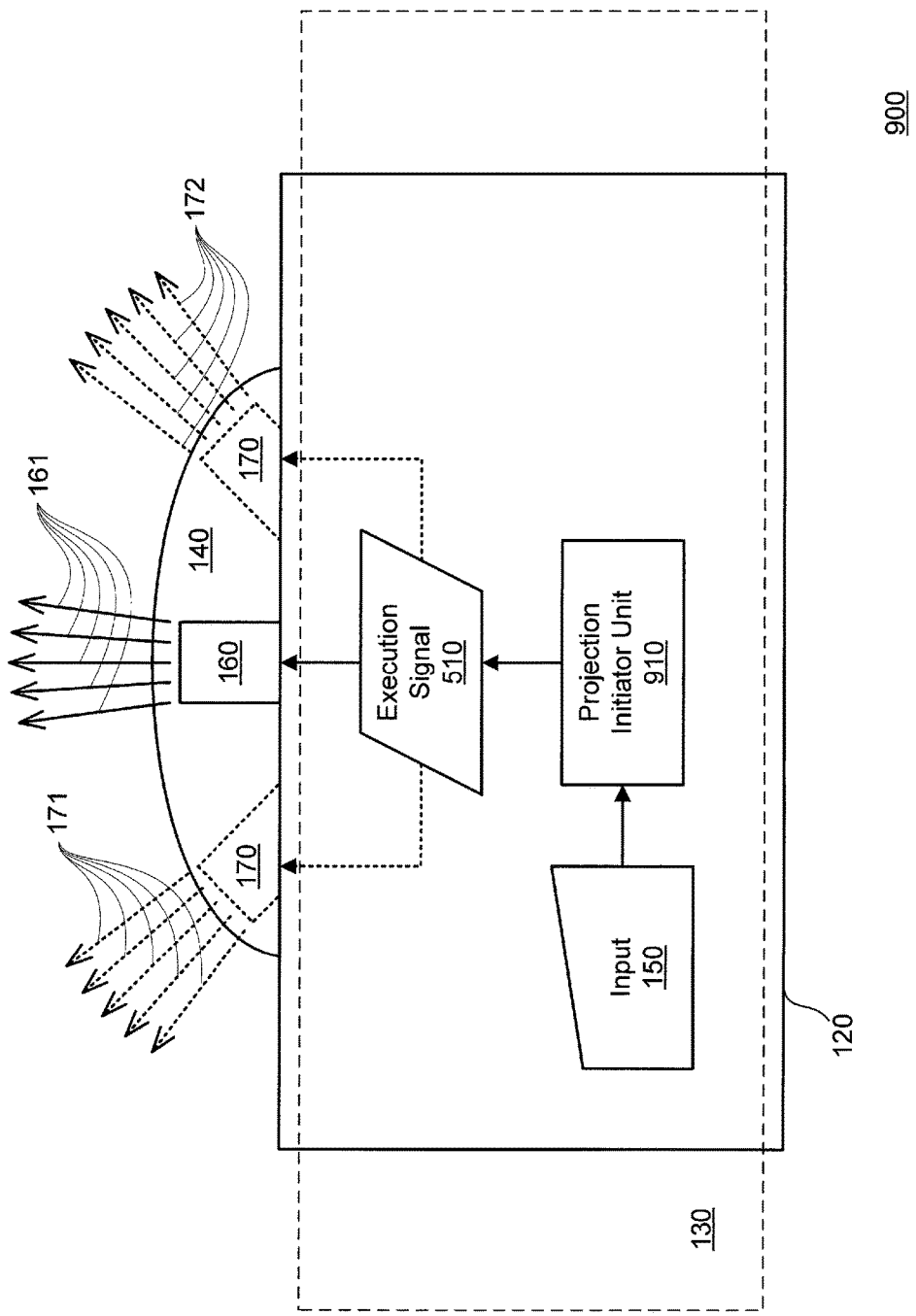
FIG. 9 is a diagram of a fourth exemplary self-defense system in accordance with an embodiment.

With reference now to FIG. 9, a fourth exemplary self-defense system 900 in accordance with an embodiment is shown. Fourth exemplary self-defense system 900 includes or comprises a defense unit 140, as in FIG. 1B, as well as a projection initiator unit 910 configured to enable a projection of one or more substances from a number of projection units associated with defense unit 140. In particular, projection initiator unit 910 is configured to sense or receive an input, such as input 150, and generate execution signal 510 based on the sensed or received input. In one embodiment, input 150 is an electronic signal resulting from a manual input caused by a selection of a manual selection mechanism and/or the sensing of a physical pressure by a pressure sensor, as will be further discussed herein. Once generated, execution signal 510 causes a defense event to be initiated, such as by communicating to defense unit 140 that one or more substances are to be projected from one or more of the implemented projection units.

Figure 10:
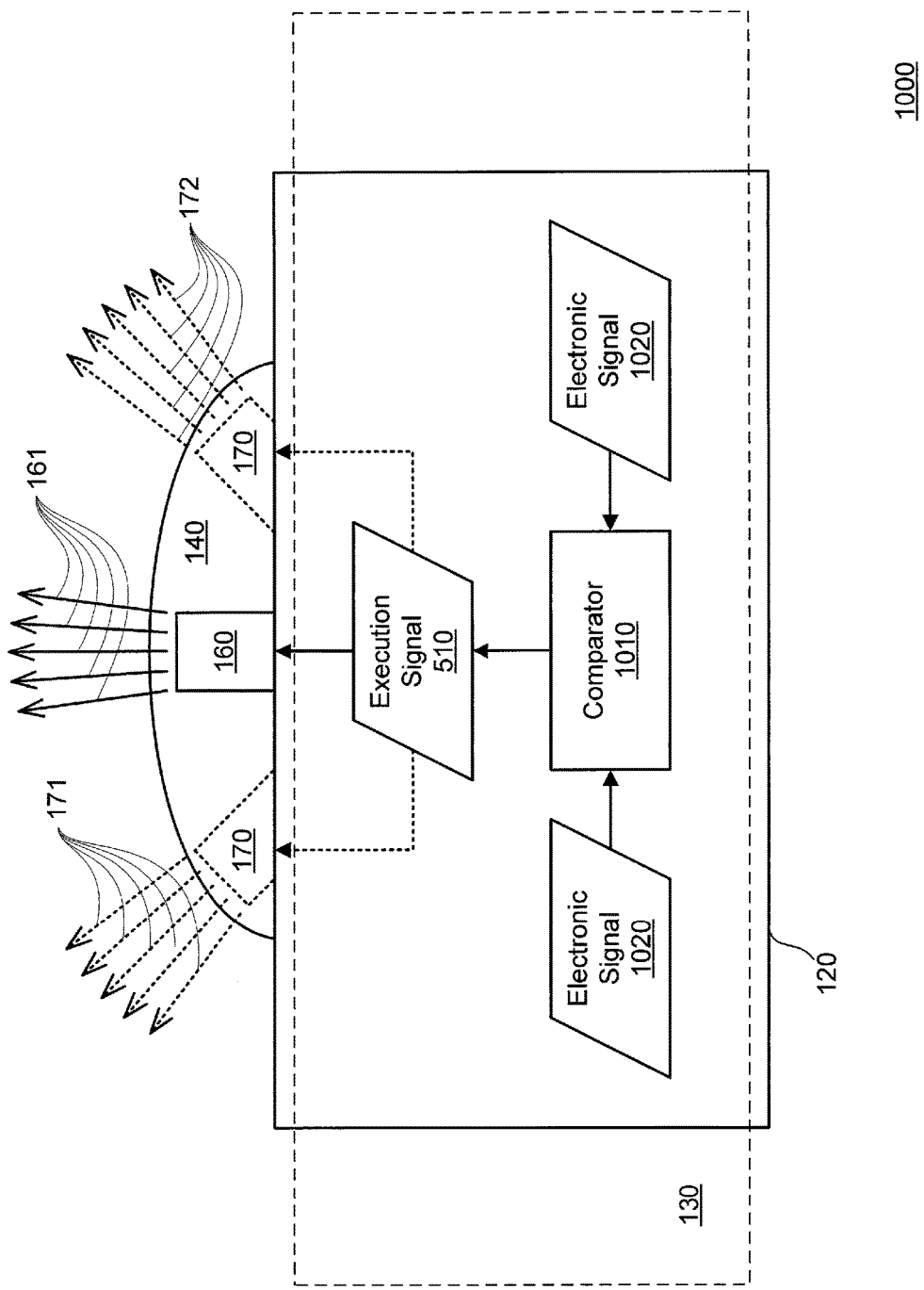
FIG. 10 is a diagram of a fifth exemplary self-defense system in accordance with an embodiment.

With reference now to FIG. 10, a fifth exemplary self-defense system 1000 in accordance with an embodiment is shown. Fifth exemplary self-defense system 1000 includes or comprises a comparator 1010 configured to conduct a comparison of two electronic signals 1020 and generate execution signal 510 based on the comparison. Additionally, defense unit 140 is configured to initiate a defense event based on execution signal 510.

Figure 6:
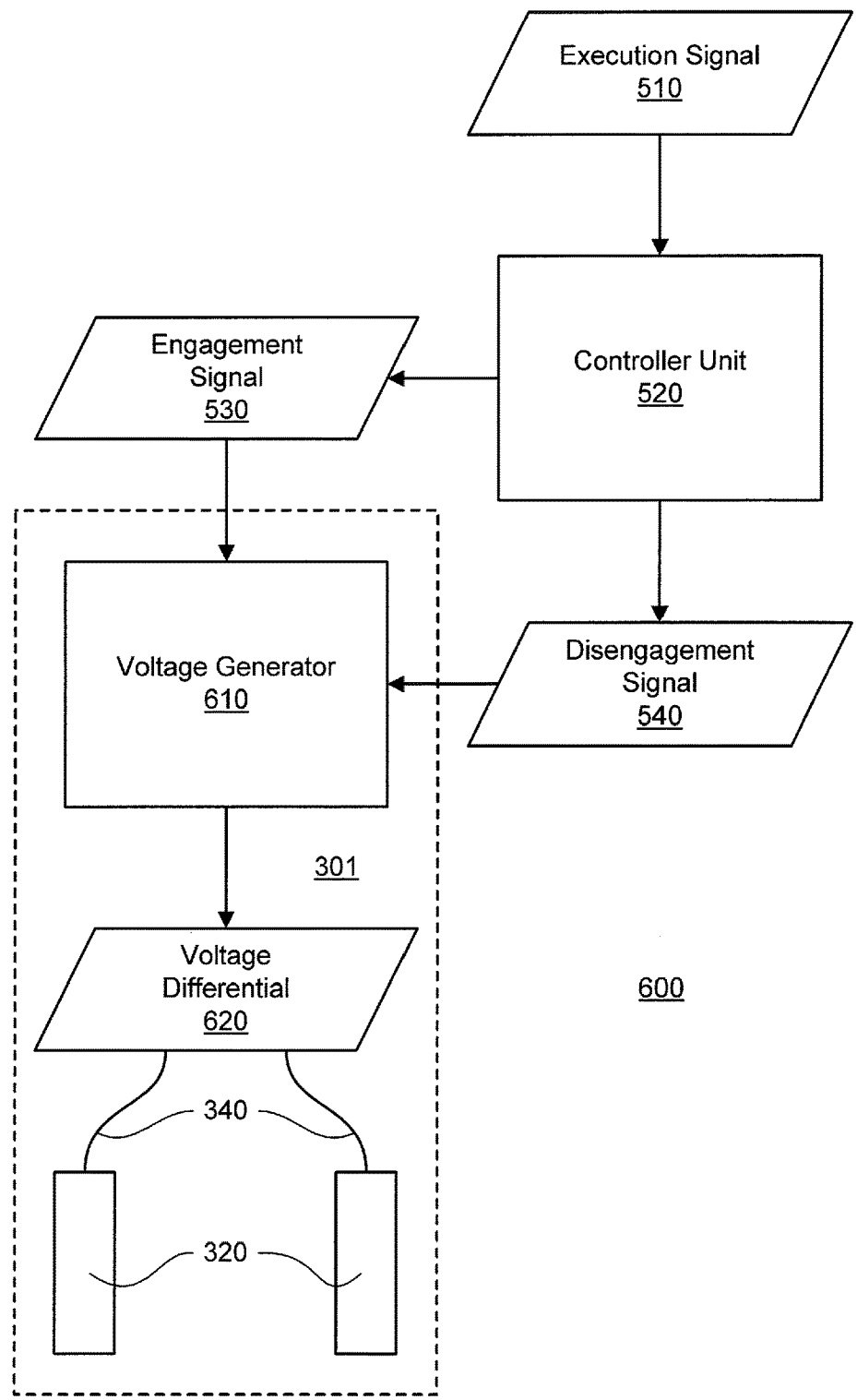
FIG. 6 is a diagram of a second exemplary engagement configuration in accordance with an embodiment.
Figure 7:
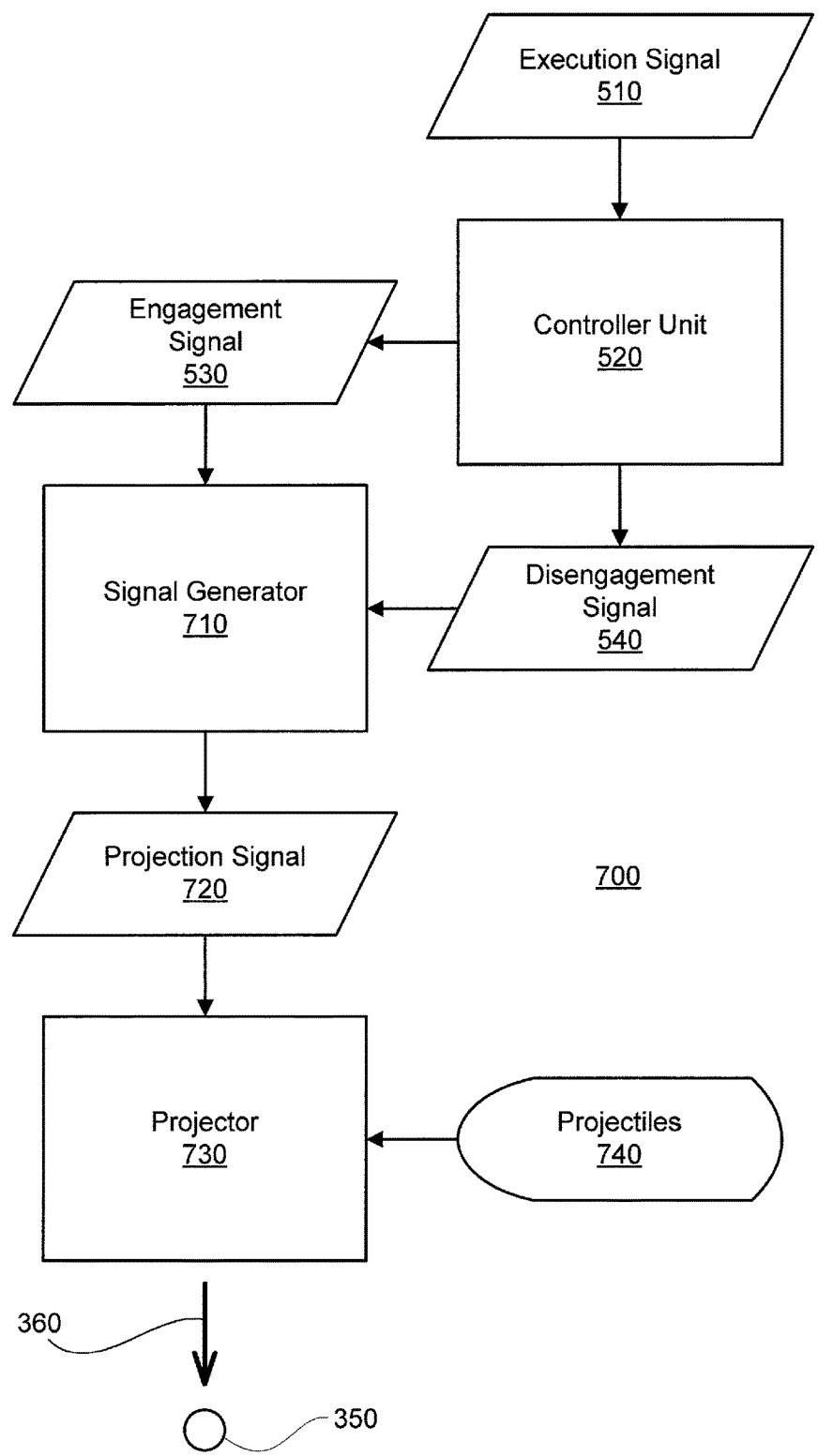
FIG. 7 is a diagram of a third exemplary engagement configuration in accordance with an embodiment.

In an embodiment, defense unit 140 includes or comprises a number of projector units each configured to project a substance based on execution signal 510. Pursuant to one embodiment, however, defense unit 140 includes or comprises a number of conductive energy devices each including or comprising two electrodes and configured to generate a voltage differential above 50 kV between their respective electrodes based on execution signal 510. See, e.g., exemplary conductive energy device 301 shown in FIGS. 3B and 6.

With reference still to FIG. 10, an embodiment provides that electronic signals 1020 are an input signal and a threshold voltage, respectively, and that each of these signals has a signal amplitude. Additionally, comparator 1010 is configured to compare the two signal amplitudes and generate execution signal 510 in response to an absolute value or magnitude of a signal amplitude of the input signal being above an absolute value or magnitude of a signal amplitude of the threshold voltage.

Figure 11:
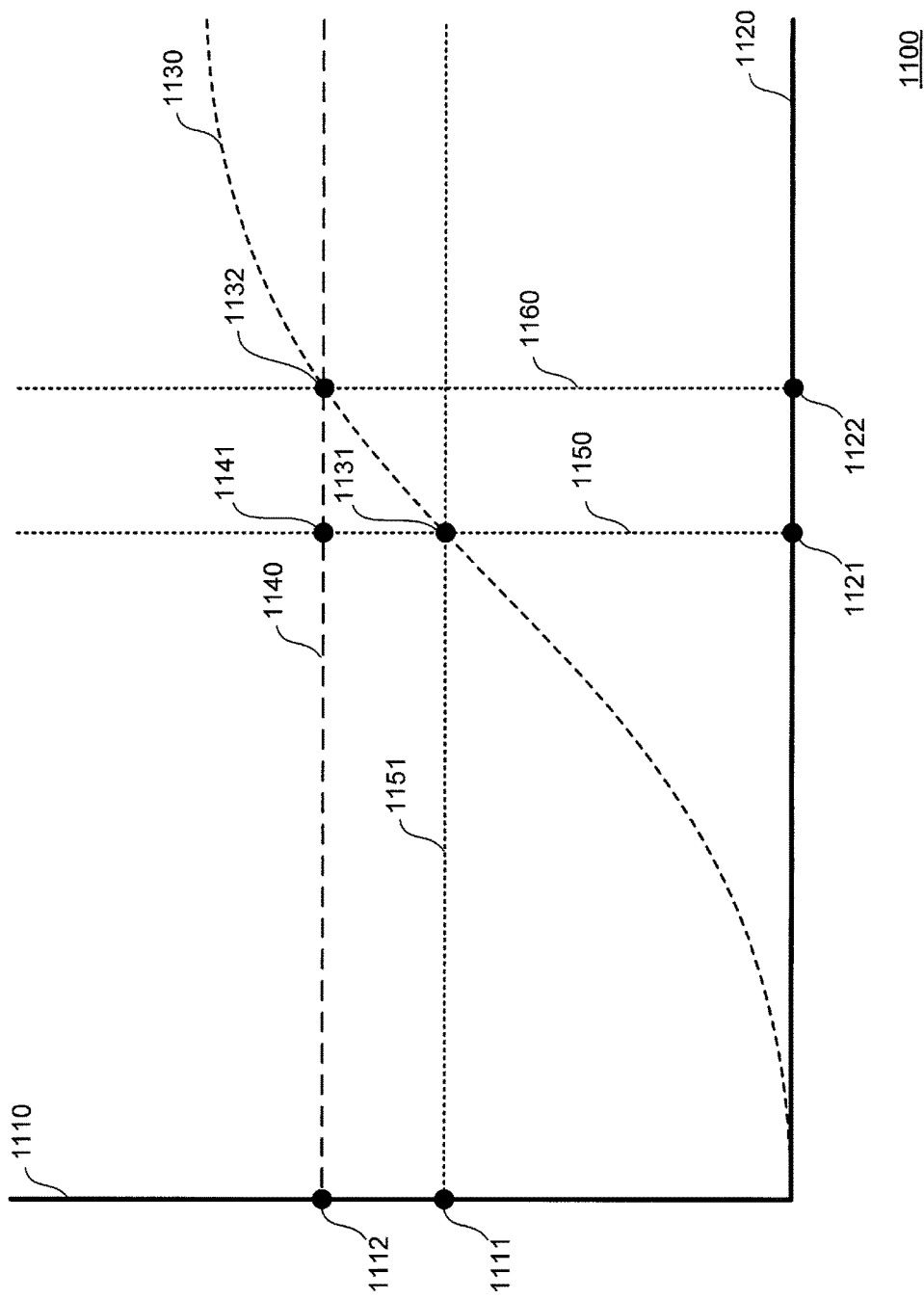
FIG. 11 is a graph of an exemplary signal comparison in accordance with an embodiment.

To further illustrate, and with reference now to FIG. 11, a graph 1100 of an exemplary signal comparison in accordance with an embodiment is shown. Graph 1100 includes or comprises voltage amplitude and time axes 1110, 1120, wherein an input signal 1130 and a threshold voltage 1140 corresponding to the two electronic signals 1020, respectively, are plotted with respect to these axes. At a first exemplary instant of time, as indicated by point 1121, it is noted that input signal 1130 has a first exemplary signal amplitude, indicated by point 1111, corresponding to coordinate 1131 (as shown by graphical axes 1150, 1151). At this same instant of time, it is noted that threshold voltage 1140, which may be the result of a direct current (DC) signal, has an exemplary threshold amplitude, indicated by point 1112, corresponding to coordinate 1141 (as shown by graphical axis 1150 and threshold voltage 1140). It may therefore be seen that the amplitude of input signal 1130 is below the amplitude of threshold voltage 1140 at the first exemplary instant of time that is indicated by point 1121. Consequently, an embodiment provides that execution signal 510 will not be generated, and that no defense event will be initiated, at this point in time.

With reference still to FIG. 11, at a second exemplary instant of time, as indicated by point 1122, it is noted that input signal 1130 has a second exemplary signal amplitude, indicated by point 1112, corresponding to coordinate 1132 (as shown by graphical axis 1160 and threshold voltage 1140). At this same instant of time, it is noted that threshold voltage 1140 has this same signal amplitude. It may therefore be seen that the amplitude of input signal 1130 equals the amplitude of threshold voltage 1140 at the second exemplary instant of time that is indicated by point 1122. Consequently, an embodiment provides that execution signal 510 will be generated at or around this latter point in time such that a defense event will be initiated.

Figure 12:
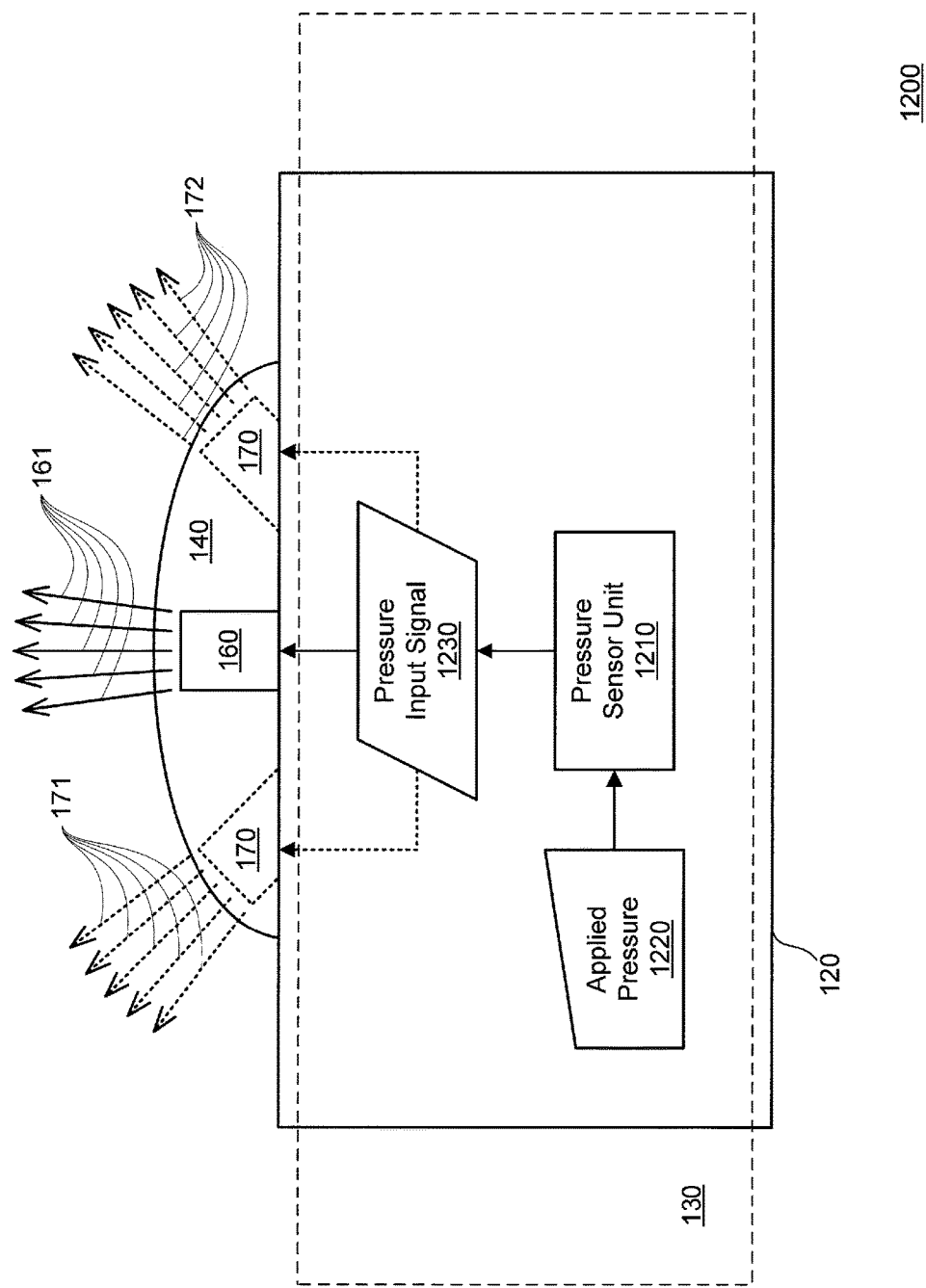
FIG. 12 is a diagram of a sixth exemplary self-defense system in accordance with an embodiment.

With reference now to FIG. 12, a sixth exemplary self-defense system 1200 in accordance with an embodiment is shown. Sixth exemplary self-defense system 1200 includes or comprises material 120, which is sized to conform to appendage 130, and a pressure sensor unit 1210 positioned to sense an applied pressure 1220 and generate a pressure input signal 1230 based on applied pressure 1220. Sixth exemplary self-defense system 1200 also includes or comprises a defense unit 140, which is coupled with material 120 and communicatively associated with pressure sensor unit 1210, such as by a wireless (e.g., using short wavelength radio transmissions) or wired communication paradigm, wherein defense unit 140 is configured to initiate a defense event based on pressure input signal 1230.

Consider the example where an attacker grabs a user's arm, wherein material 120 is wrapped around the user's arm. The physical pressure (e.g., applied pressure 1220) applied by the attacker to material 120 is sensed by pressure sensor unit 1210. In response to sensing this pressure, pressure sensor unit 1210 generates pressure input signal 1230, wherein pressure input signal 1230 is an electronic, electromagnetic or optical signal that causes defense unit 140 to initiate a defense event.

In one embodiment, defense unit 140 includes or comprises projector unit 160, which is coupled with material 120 and positioned to project a substance in a first direction based on pressure input signal 1230. Defense unit 140 may also include or comprise a second projector unit (e.g., one or more additional projector units 170) coupled with material 120 and positioned to project a substance in a second direction based on pressure input signal 1230 when projector unit 160 projects a substance in the first direction, wherein the first projector unit is incapable of simultaneously projecting a substance in both of the first and second directions. In this manner, multiple defense units may be implemented to increase an effective range of a defense event.

Furthermore, in one embodiment, pressure sensor unit 1210 and defense unit 140 include, comprise or are integrated with a wireless transmitter and a wireless receiver, respectively. When pressure sensor unit 1210 senses applied pressure 1220, pressure input signal 1230 is wirelessly routed to defense unit 140. In this manner, one or more pressure sensors associated with pressure sensor unit 1210 may be positioned at different locations on a user's body, or elsewhere.

Figure 13:
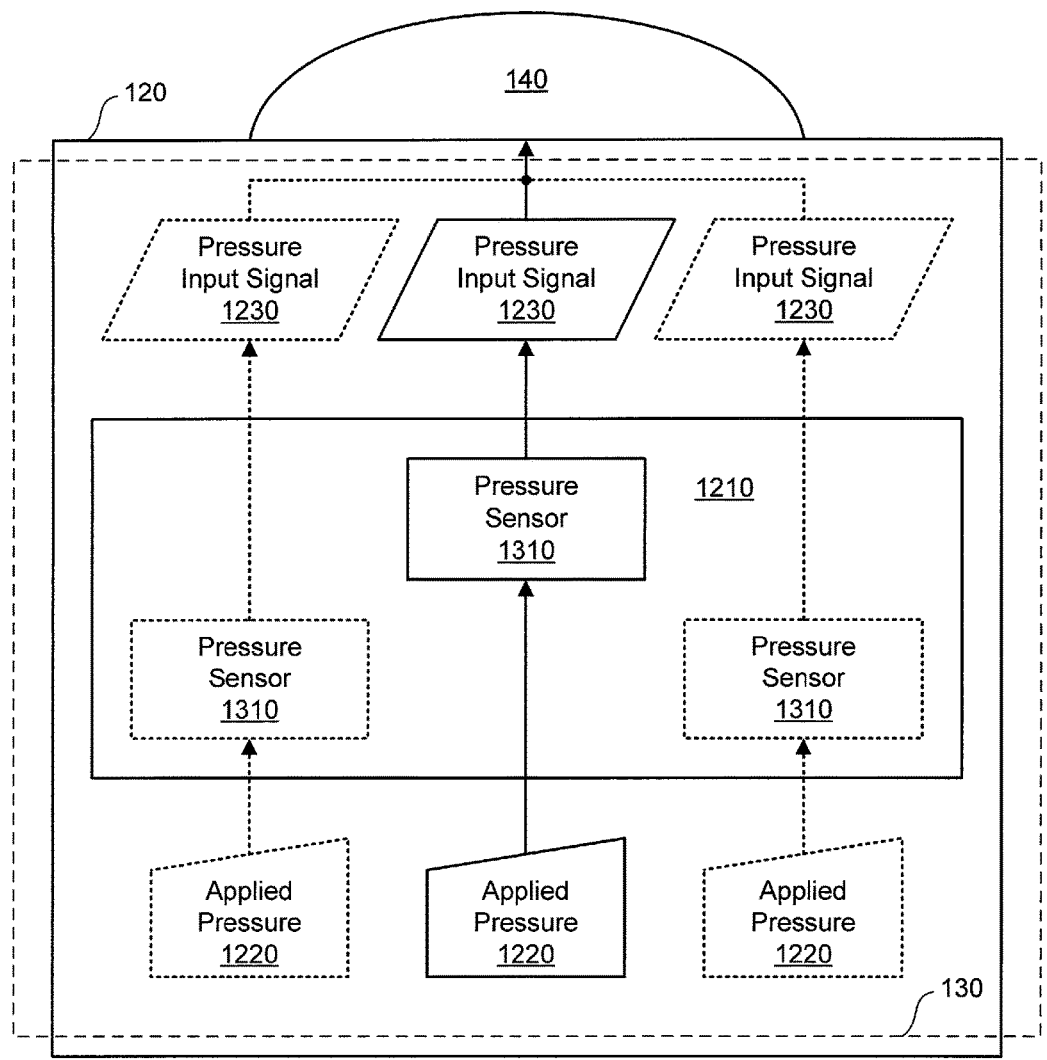
FIG. 13 is a diagram of a seventh exemplary self-defense system in accordance with an embodiment.

With reference now to FIG. 13, a seventh exemplary self-defense system 1300 in accordance with an embodiment is shown. Seventh exemplary self-defense system 1300 includes or comprises one or more pressure sensors 1310 coupled or associated with pressure sensor unit 1210. Each of the one or more pressure sensors 1310 is positioned to sense an applied pressure 1220 and generate a pressure input signal 1230 based on the applied pressure 1220 sensed by that sensor, wherein each of the one or more pressure input signals 1230 has a signal amplitude. In this manner, multiple pressure sensors may be located at different positions such that a probability of sensing an applied pressure by at least one sensor is increased. Moreover, an embodiment provides that a defense event is initiated in response to at least two different pressure sensors detecting applied pressures above a predetermined pressure threshold so as to minimize the probability of initiating a defense event in response to a false positive, which could occur, for example, when one of the pressure sensors is accidentally hit or otherwise triggered.

Figure 14:
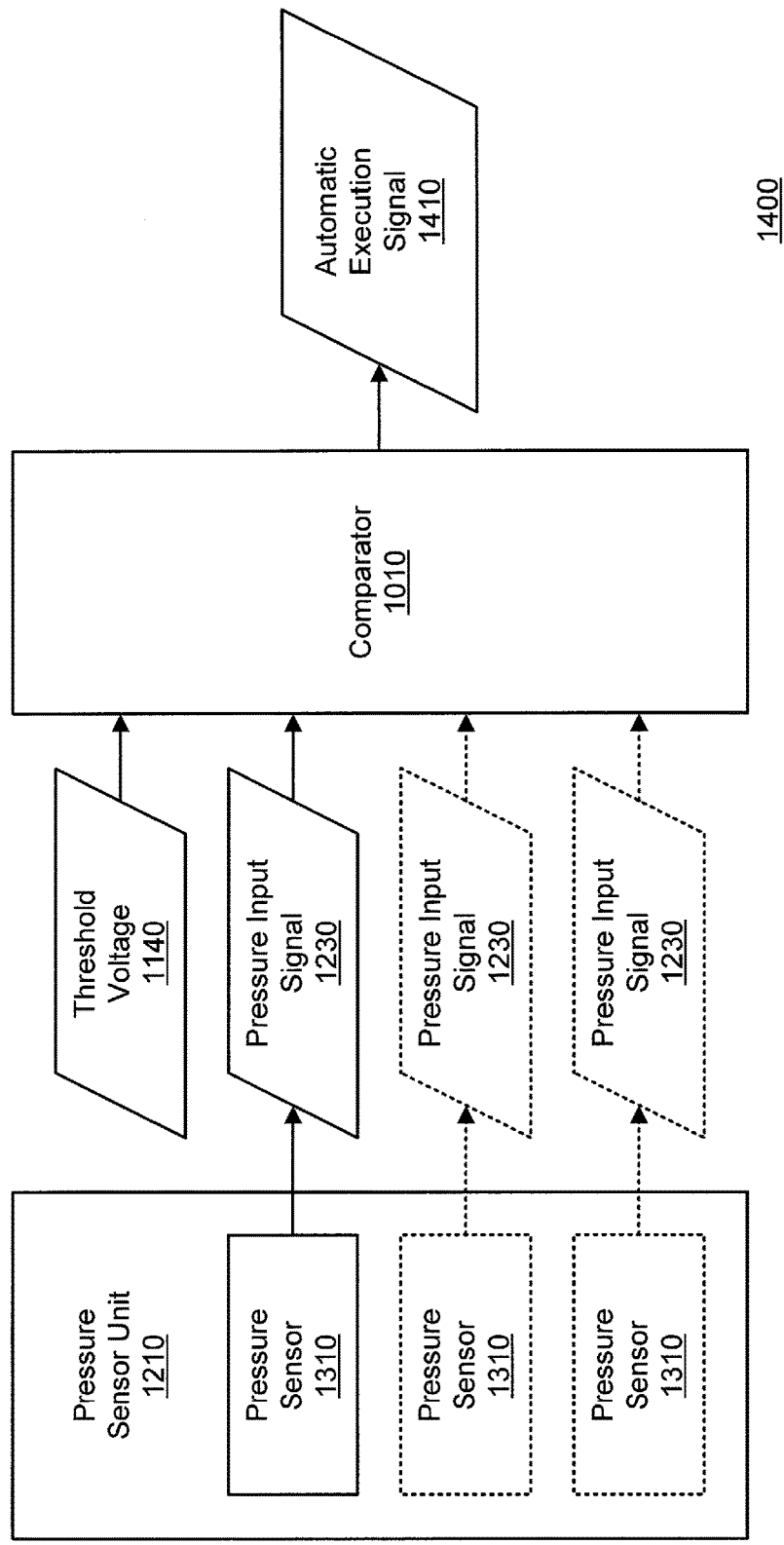
FIG. 14 is a diagram of a first exemplary signal comparison system in accordance with an embodiment.

To further illustrate, and with reference now to FIG. 14, a first exemplary signal comparison system 1400 in accordance with an embodiment is shown. In particular, a comparator 1010 is associated with the one or more pressure sensors, wherein comparator 1010 is positioned to compare the one or more pressure input signals 1230 with a threshold voltage 1140 and generate an automatic execution signal 1410 in response to an absolute value or magnitude of one or more (e.g., at least one, at least two, at least three, etc.) of the signal amplitudes of the one or more pressure input signals 1230 being above an absolute value or magnitude of threshold voltage 1140. Moreover, defense unit 140 is configured to initiate a defense event based on automatic execution signal 1410.

For purposes of clarity, it is noted that automatic execution signal 1410 may or may not be the same signal as execution signal 510 discussed herein. However, an embodiment provides that automatic execution signal 1410 is in fact distinguishable from a manual execution signal, as discussed infra.

The foregoing notwithstanding, it is noted that inputs other than applied physical pressures may be indicative of an attack. For example, a user's own behavior and physiological state may indicate that the user is in danger. In particular, a user's heart rate may become substantially elevated in a relatively short period of time in response to the fear and adrenaline associated with a sudden attack, wherein such a rapid increase in heart rate is distinguishable from slower heart rate elevations corresponding to conditions associated with normal degrees of human exercise. As such, an embodiment provides that a user's heart rate is monitored and utilized as an input in determining whether a defense event is to be initiated.

Figure 15:
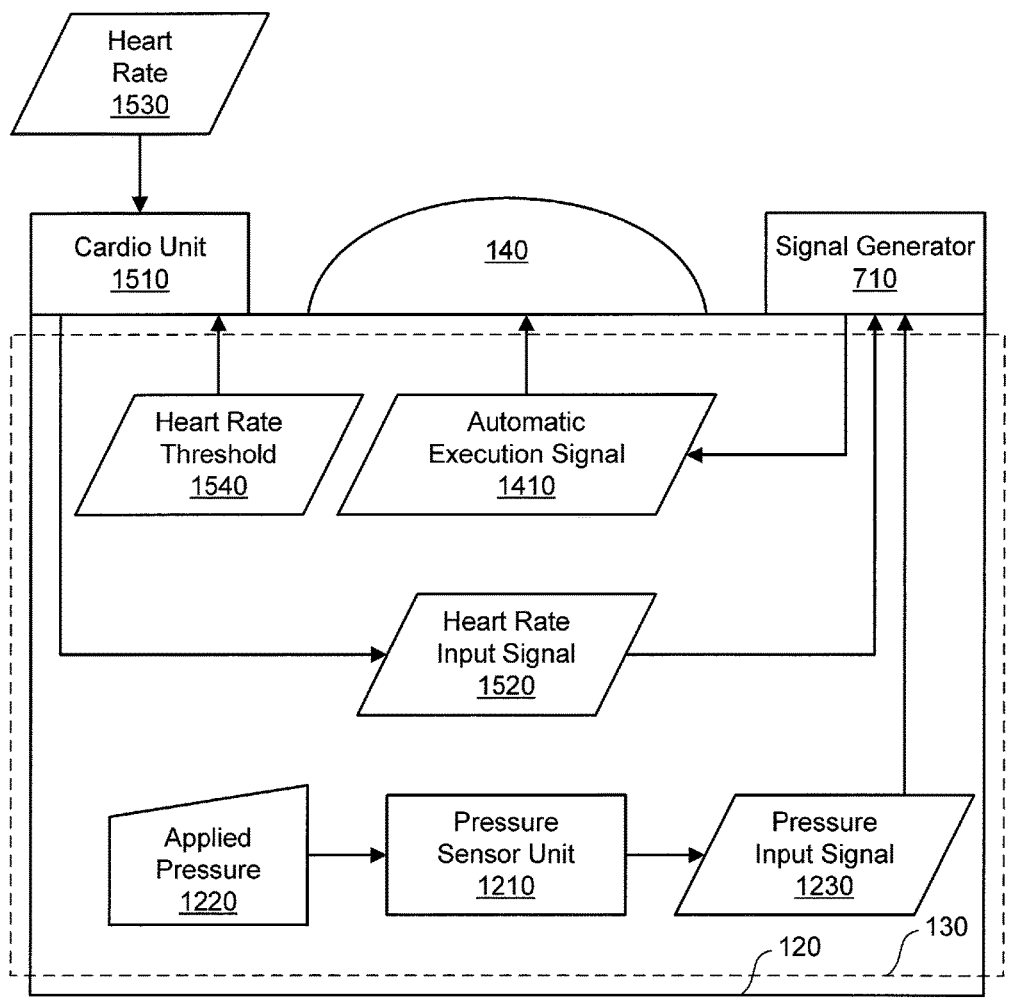
FIG. 15 is a diagram of an eighth exemplary self-defense system in accordance with an embodiment.

To illustrate, and with reference now to FIG. 15, an eighth exemplary self-defense system 1500 in accordance with an embodiment is shown. Eighth exemplary self-defense system 1500 includes or comprises a cardio unit 1510 configured to generate a heart rate input signal 1520, which may be an electronic signal, in response to a detected heart rate 1530 being above a heart rate threshold. Eighth exemplary self-defense system 1500 also includes or comprises a signal generator 710 configured to generate automatic execution signal 1410 based on pressure input signal 1230 and/or heart rate input signal 1520. Moreover, defense unit 140 is positioned to initiate a defense event based on automatic execution signal 1410.

Thus, in an embodiment, a defense event is initiated in response to a detected heart rate 1530 being above a heart rate threshold. However, in order to minimize false positives, one embodiment provides that a defense event is initiated in response to two different conditions occurring, such as when (1) a detected heart rate 1530 is above a heart rate threshold 1540 and (2) pressure sensor unit 1210 senses an applied pressure 1220 above a predetermined pressure threshold.

Figure 16:
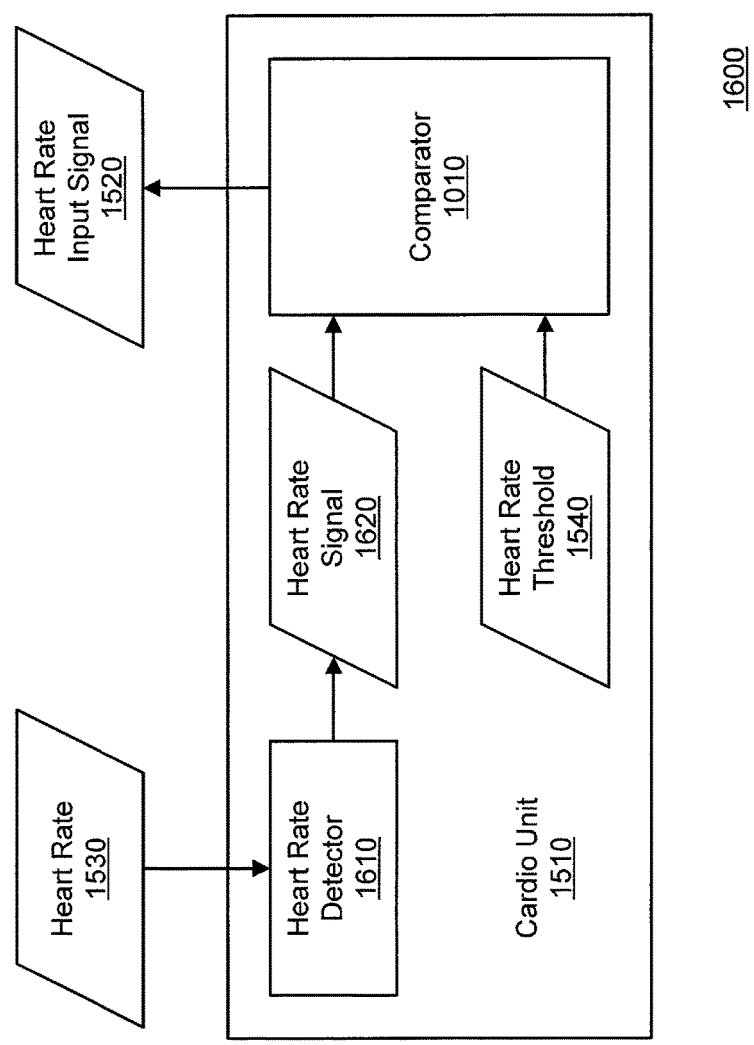
FIG. 16 is a diagram of a second exemplary signal comparison system in accordance with an embodiment.

With reference now to FIG. 16, a second exemplary signal comparison system 1600 in accordance with an embodiment is shown. Second exemplary signal comparison system 1600 includes or comprises a heart rate detector 1610 coupled or associated with cardio unit 1510 and configured to detect heart rate 1530 and generate a heart rate signal 1620, which may be an electronic signal, based on heart rate 1530. Second exemplary signal comparison system 1600 also includes or comprises a comparator 1010 coupled or associated with heart rate detector 1610, wherein comparator 1010 is configured to conduct a comparison between heart rate signal 1620 and heart rate threshold 1540. Comparator is also configured to generate heart rate input signal 1520, based on the comparison, when an absolute value or magnitude of heart rate signal 1620 exceeds an absolute value or magnitude of heart rate threshold.

In addition to the foregoing, it is noted that ambient audio data may be indicative of an attack. For example, a user may spontaneously utter terms such as "stop" or "help" in response to being attacked. As a second example, a gunshot or other sounds associated with threatening behavior may be indicative of an attack. As such, an embodiment provides that various preselected audio cues are implemented to monitor ambient audio data and determine whether a defense event is to be initiated.

Figure 17:
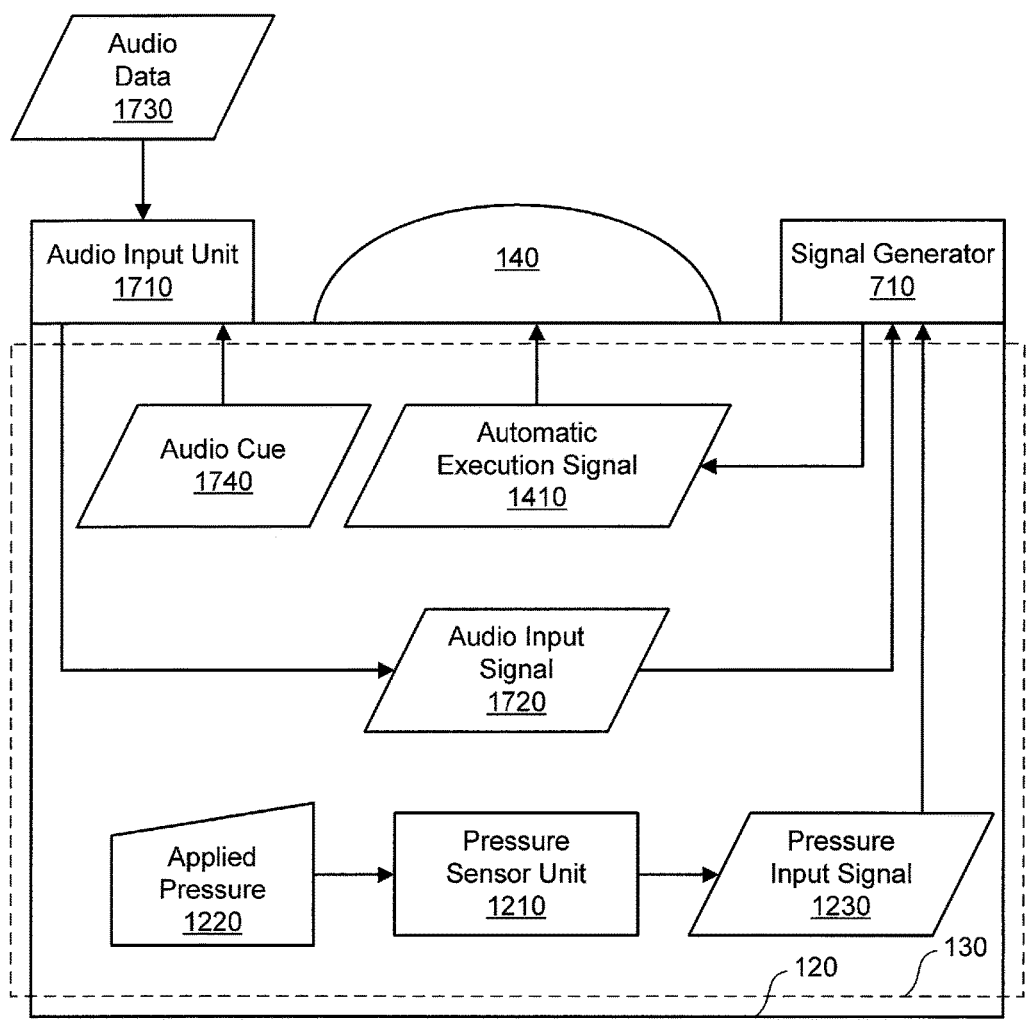
FIG. 17 is a diagram of a ninth exemplary self-defense system in accordance with an embodiment.

To illustrate, and with reference now to FIG. 17, a ninth exemplary self-defense system 1700 in accordance with an embodiment is shown. Ninth exemplary self-defense system 1700 includes or comprises an audio input unit 1710 configured to generate an audio input signal 1720 in response to detected audio data 1730 corresponding to a preselected audio cue 1740. Ninth exemplary self-defense system 1700 also includes or comprises a signal generator 710 coupled or associated with pressure sensor unit 1210 and audio input unit 1710, wherein signal generator 710 is configured to generate automatic execution signal 1410 based on pressure input signal 1230 and/or audio input signal 1720. Moreover, defense unit 140 is positioned to initiate a defense event based on automatic execution signal 1410.

Figure 18:
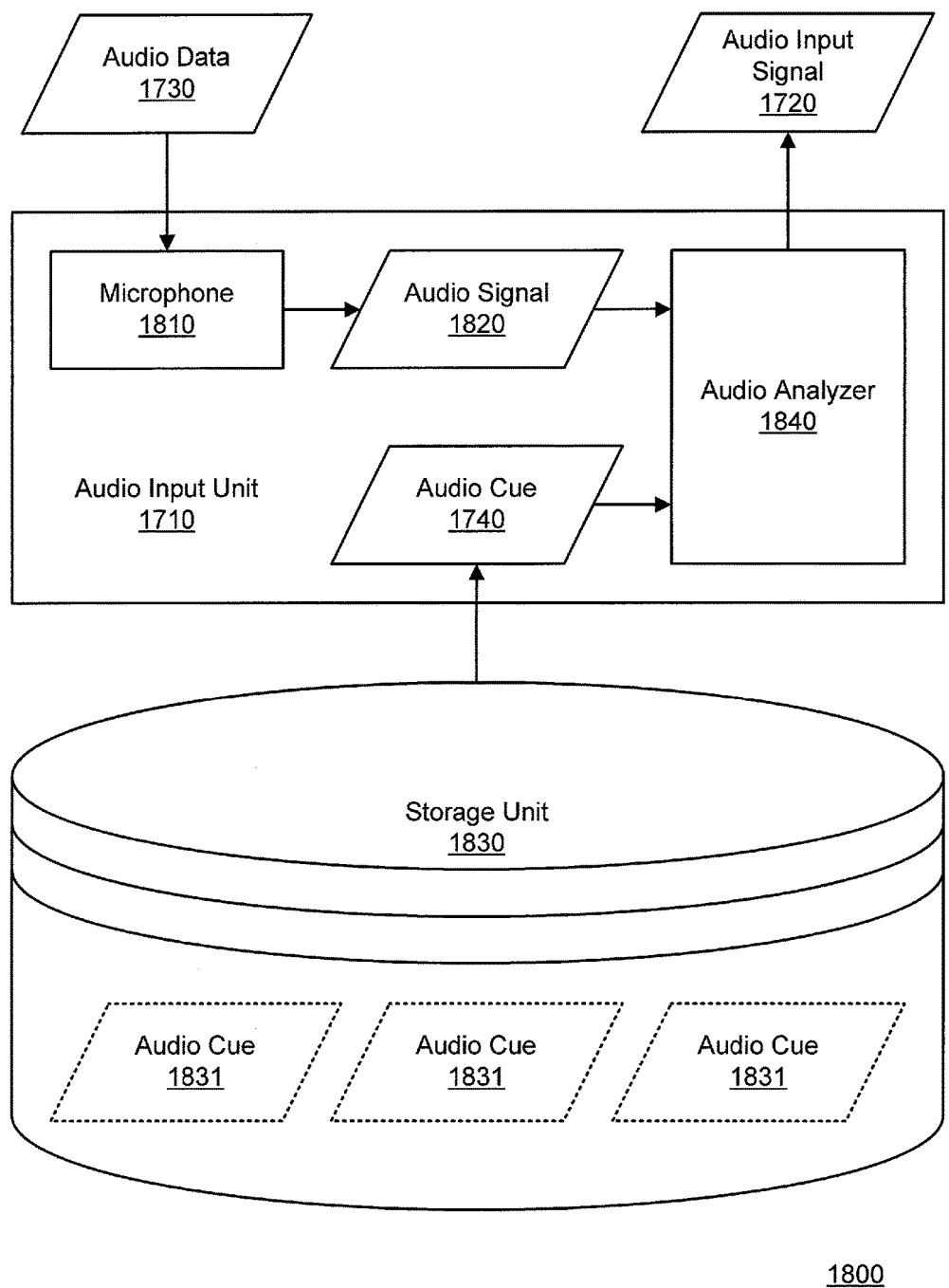
FIG. 18 is a diagram of a third exemplary signal comparison system in accordance with an embodiment.

With reference now to FIG. 18, a third exemplary signal comparison system 1800 in accordance with an embodiment is shown. In particular, a microphone 1810 is coupled or associated with audio input unit 1710 and positioned to detect audio data 1730 and generate an audio signal 1820, which may be an electronic signal, based on audio data 1730. Additionally, a storage unit 1830 is associated with audio input unit 1710 and configured to store a number of preselected audio cues 1831. Moreover, an audio analyzer 1840 is coupled or associated with storage unit 1830, wherein audio analyzer 1840 is configured to access audio cue 1740 from storage unit 1830, conduct a comparison between audio signal 1820 and audio cue 1740, and generate audio input signal 1720 based on the comparison, such as when audio signal 1820 substantially matches or corresponds to audio cue 1740.

The foregoing notwithstanding, it may be beneficial to enable a user to manually initiate a defense event based on the user's own judgment. As such, and with reference now to FIG. 19, a tenth exemplary self-defense system 1900 in accordance with an embodiment is shown. Tenth exemplary self-defense system 1900 includes or comprises a manual selector 1910 coupled or associated with defense unit 140 and positioned to generate a manual execution signal 1920 in response to a selection 1930 of manual selector 1910. Manual execution signal 1920 is then routed to defense unit 140, which automatically initiates a defense event when manual execution signal 1920 is received. Furthermore, an embodiment provides that both pressure sensor unit 1210 and manual selector 1910 are implemented such that a defense event will be initiated in response to either of pressure input signal 1230 or manual execution signal 1920 being generated.

With reference now to FIG. 20A, a first exemplary logic system 2000 in accordance with an embodiment is shown. First exemplary logic system 2000 includes or comprises an OR gate 2010 configured to generate execution signal 510 when either manual execution signal 1920 or pressure input signal 1230 have a signal amplitude corresponding to a logical "1". It is noted that projector unit 160, and optionally one or more additional projector units 170, are configured to initiate a defense event in response to execution signal 510 being generated by OR gate 2010. In this manner, an embodiment provides that a defense event is initiated based on either (1) a selection 1930 of manual selector 1910 or (2) applied pressure 1220 being above a preselected pressure threshold.

With reference now to FIG. 20B, a second exemplary logic system 2001 in accordance with an embodiment is shown. Second exemplary logic system 2001 is substantially similar to first exemplary logic system 2000, except that an XOR gate 2020 is implemented. For example, when either manual execution signal 1920 or pressure input signal 1230 have a signal amplitude corresponding to a logical "0", XOR gate 2020 generates execution signal 510. Thus, it is noted that different logic gates (e.g., AND and NAND gates) and electronic components may be implemented to generate execution signal 510 based on a number of input signals. Indeed, OR and XOR gates 2010, 2020 are presented as exemplary logic gates, and are not meant to narrow the scope of the present technology.

Thus, and with reference still to the exemplary embodiments shown in FIGS. 19, 20A and 20B, a defense event may be manually initiated when a user selects manual selector 1910 or automatically initiated when an applied pressure 1220 above a predetermined pressure threshold is sensed by pressure sensor unit 1210. Indeed, various embodiments may be implemented such that a defense event is initiated in response to a manual user input, or in response to a different input (such as the exemplary inputs discussed herein). However, other embodiments may also be implemented.

Figure 21A:
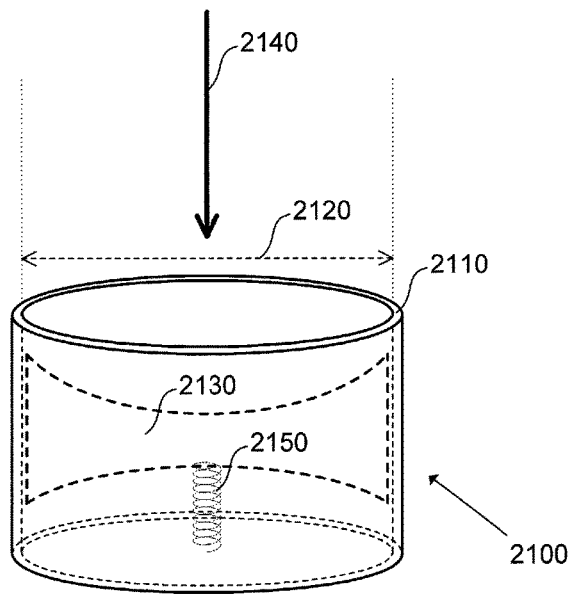
FIGS. 21A and 21B are diagrams of an exemplary manual selector in accordance with an embodiment.
Figure 21B:
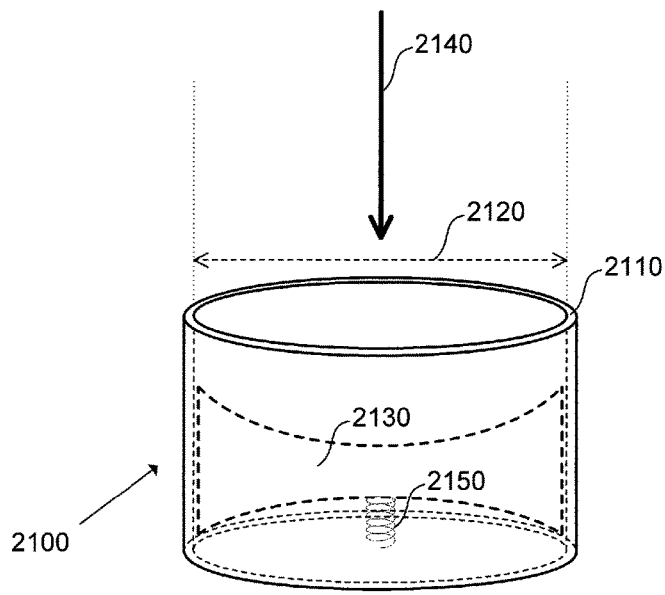

With reference now to FIGS. 21A and 21B, an exemplary manual selector 2100 in accordance with an embodiment is shown. Exemplary manual selector 2100 includes or comprises a digit receptacle 2110 having a width or diameter 2120 based on a preselected digit width or diameter. Exemplary manual selector 2100 also includes or comprises a selection mechanism 2130 configured to move from a first position, as shown in FIG. 21A, to a second position, as shown in FIG. 21B, within digit receptacle 2110, wherein manual execution signal 1920 is generated when selection mechanism 2130 is in the second position.

For example, when a user sticks his or her finger inside digit receptacle 2110 and pushes on selection mechanism 2130 in an exemplary selection direction 2140, selection mechanism 2130 is displaced from a first position to a second position toward an elastic or spring member 2150. Once in this second position, an electronic switch associated with selection mechanism 2130 is activated or closed such that manual execution signal 1920 is generated, which in turn causes a defense event to be initiated. Moreover, once the force applied to selection mechanism 2130 in exemplary selection direction 2140 is decreased below the opposing force applied on selection mechanism 2130 by elastic or spring member 2150, selection mechanism 2130 returns to the first position such that exemplary manual selector 2100 is reset. Furthermore, one embodiment provides that an initiated defense event is halted or terminated once selection mechanism 2130 returns to the first position.

The foregoing notwithstanding, it is noted that, in accordance with an embodiment, digit receptacle 2110 and selection mechanism 2130 are sized to prevent an unintended or accidental selection of selection mechanism 2130. For example, as shown in FIG. 21A, a portion of digit receptacle 2110 extends beyond selection mechanism 2130 when selection mechanism 2130 is in the first position, and width or diameter 2120 of digit receptacle 2110 is based on a known finger width, such that an unintended or accidental selection of selection mechanism 2130 is minimized.

Figure 22:
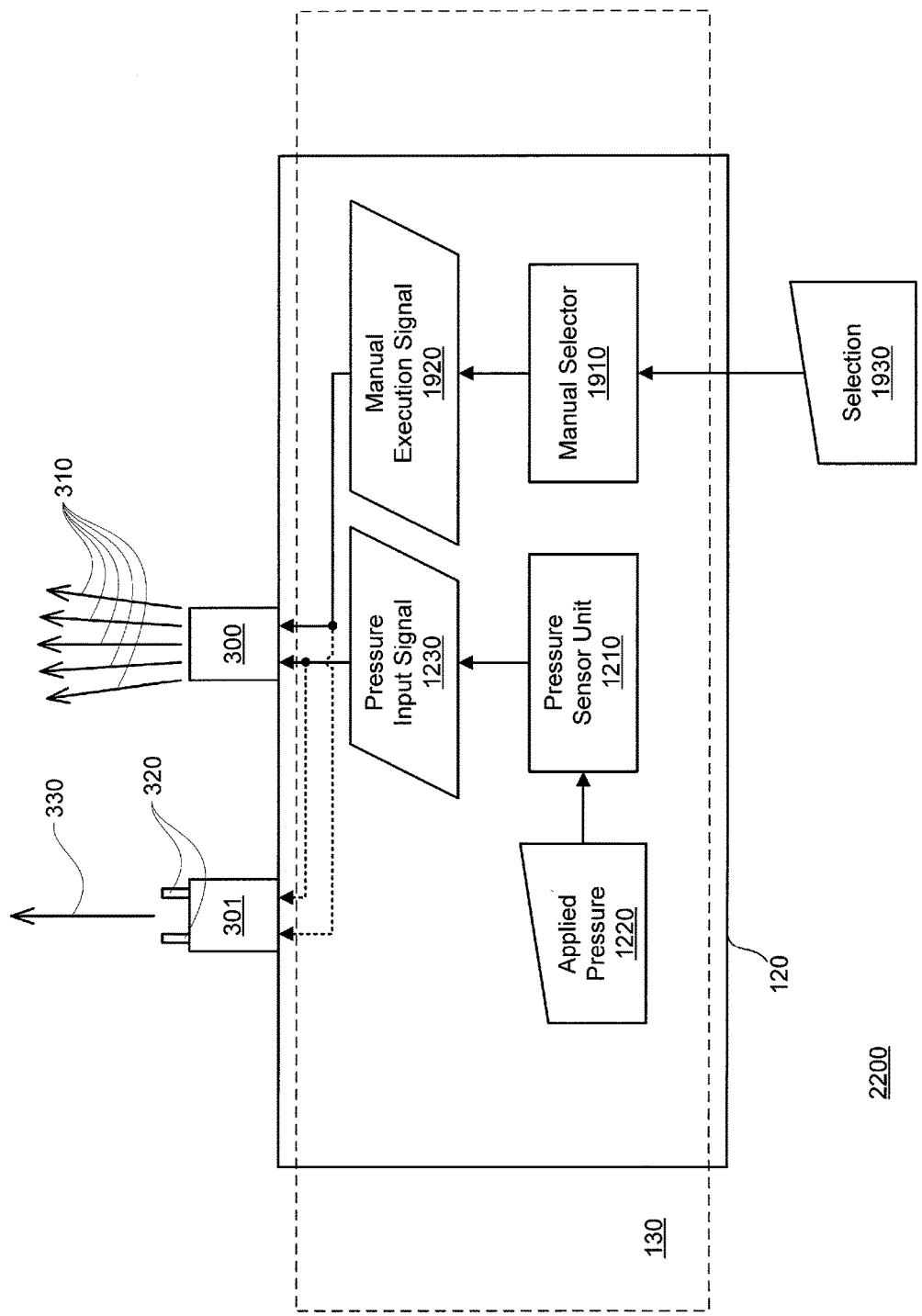
FIG. 22 is a diagram of an eleventh exemplary self-defense system in accordance with an embodiment.

With reference now to FIG. 22, an eleventh exemplary self-defense system 2200 in accordance with an embodiment is shown. Eleventh exemplary self-defense system 2200 includes or comprises a conductive energy device 301 coupled with material 120 and including or comprising two electrodes 320. Conductive energy device 301 is configured to generate a voltage differential between electrodes 320 based on pressure input signal 1230 or manual execution signal 1920. Pursuant to one embodiment, this voltage differential is in the range of approximately 50 to 1000 kilovolts (kV).

In addition to the foregoing, an embodiment provides that eleventh exemplary self-defense system 2200 also includes or comprises a projector unit 300 coupled with material 120 and positioned to project a substance based on pressure input signal 1230 or manual execution signal 1920. Thus, it is noted that combinations of different types of defense devices (e.g., stun guns and chemical sprayers) may be combined in a single configuration to potentially increase an effectiveness of an initiated defense event.

Figure 23A:
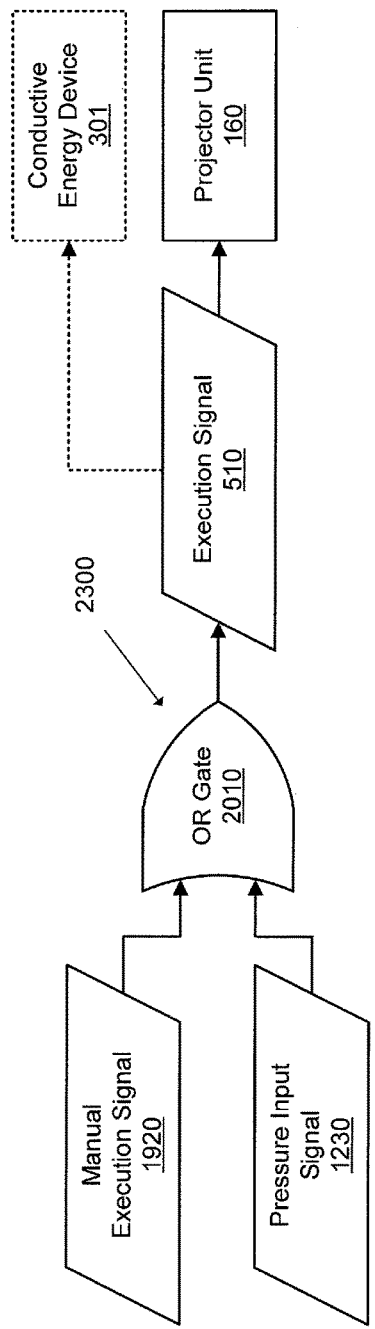
FIG. 23A is a diagram of a third exemplary logic system in accordance with an embodiment.
Figure 23B:
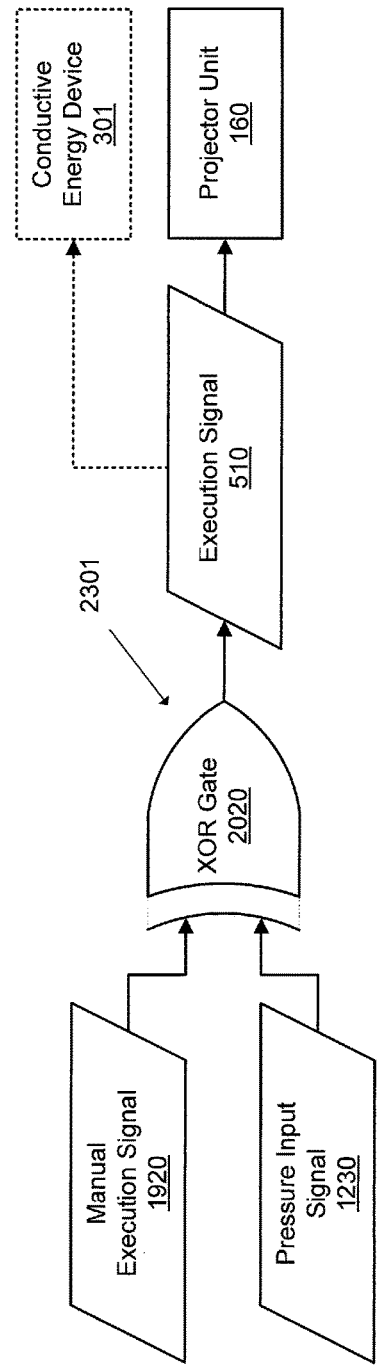
FIG. 23B is a diagram of a fourth exemplary logic system in accordance with an embodiment.

With reference now to FIGS. 23A and 23B, third and fourth exemplary logic systems 2300, 2301 in accordance with a number of exemplary embodiments are shown. Third and fourth exemplary logic systems 2300, 2301 are substantially similar to first and second exemplary logic systems 2000, 2001, respectively (see the discussions above regarding FIGS. 20A and 20B). However, in accordance with an embodiment, execution signal 510 may be implemented to cause conductive energy device 301 to initiate a defense event. Indeed, one embodiment provides that execution signal 510 causes both projector unit 160 and conductive energy device 301 to initiate a defense event at approximately the same time.

The foregoing notwithstanding, it is noted that certain information pertaining to an attack may be important to helping law enforcement detectives to identify an attacker, as well as to helping medical responders and law enforcement officers to locate the victim in a timely fashion. This information may include, but is not limited to, an attacker's voice, an image of the attacker and/or other clues, video footage of the attack, and a real-time geographic location of the attack, the latter aspect being important to quickly locating the victim so as to render protection and medical aid. In view of the foregoing, a number of embodiments will now be discussed wherein, during an initiated defense event, specific information is captured, recorded and/or transmitted to one or more preselected entities, such as a local law enforcement agency and emergency medical responders.

Figure 24:
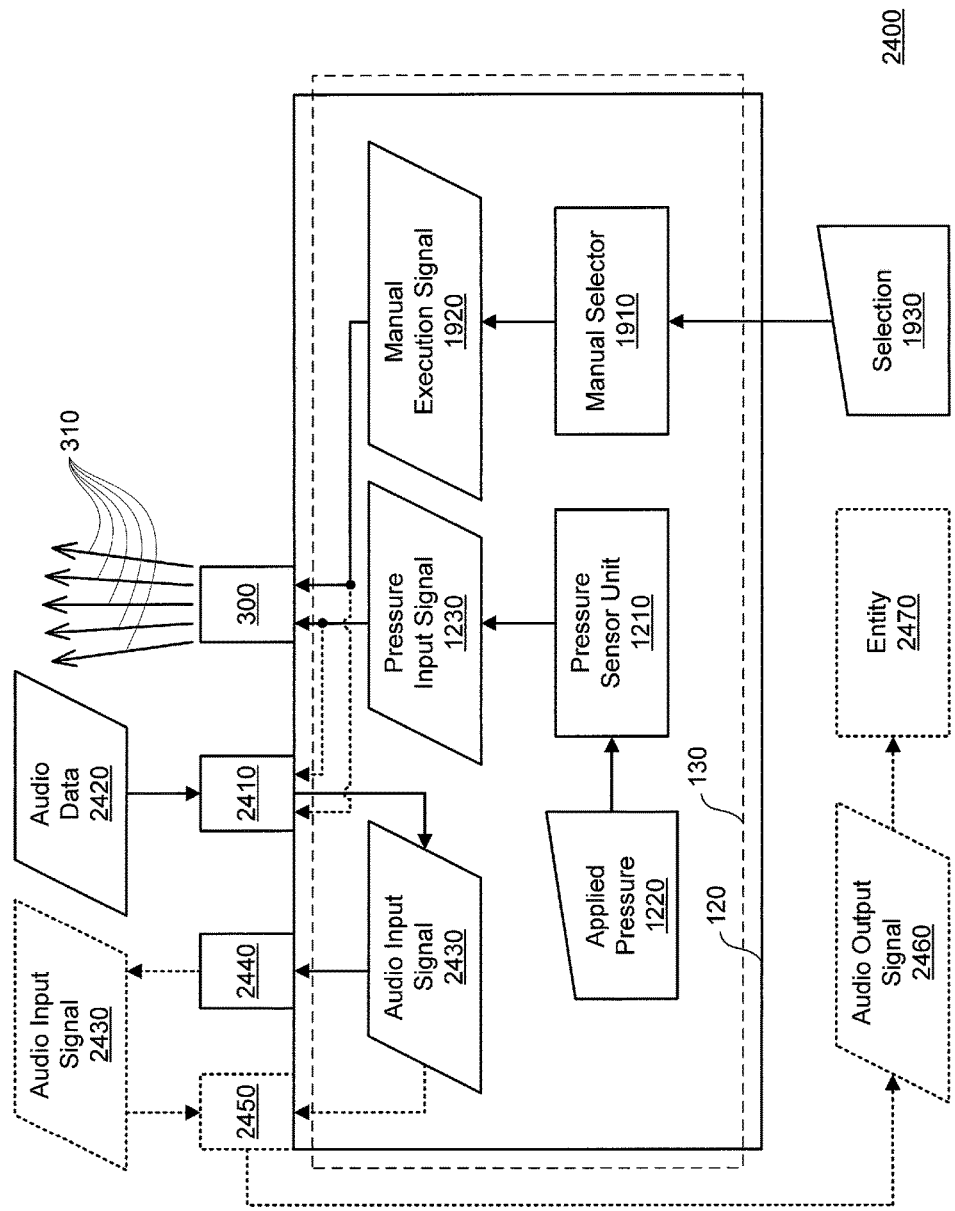
FIG. 24 is a diagram of a twelfth exemplary self-defense system in accordance with an embodiment.

With reference now to FIG. 24, a twelfth exemplary self-defense system 2400 in accordance with an embodiment is shown. Twelfth exemplary self-defense system 2400 includes or comprises an audio input unit 2410 (e.g., a microphone) positioned to capture audio data 2420 as a result of pressure input signal 1230 or manual execution signal 1920 by sensing audio data 2420 and generating an audio input signal 2430 based on or associated with audio data 2420. Twelfth exemplary self-defense system 2400 also includes or comprises a storage unit 2440 associated with audio input unit 2410 and positioned to store audio input signal 2430.

Furthermore, in an embodiment, twelfth exemplary self-defense system 2400 optionally includes or comprises a transmitter 2450 associated with audio input unit 2410 and positioned to automatically generate an audio output signal 2460 corresponding to audio input signal 2430 and automatically transmit audio output signal 2460 to a preselected entity 2470. It is noted that transmitter 2450 may be configured to receive audio input signal 2430 from either audio input unit 2410 or storage unit 2440.

With reference now to FIGS. 25A and 25B, fifth and sixth exemplary logic systems 2500, 2501 in accordance with a number of exemplary embodiments are shown. Fifth and sixth exemplary logic systems 2500, 2501 are substantially similar to first and second exemplary logic systems 2000, 2001, respectively (see the discussions above regarding FIGS. 20A and 20B). However, in accordance with an embodiment, execution signal 510 may be implemented to cause audio input unit 2410 to initiate a defense event. Indeed, one embodiment provides that execution signal 510 causes both projector unit 160 and audio input unit 2410 to initiate a defense event at approximately the same time.

Figure 26:
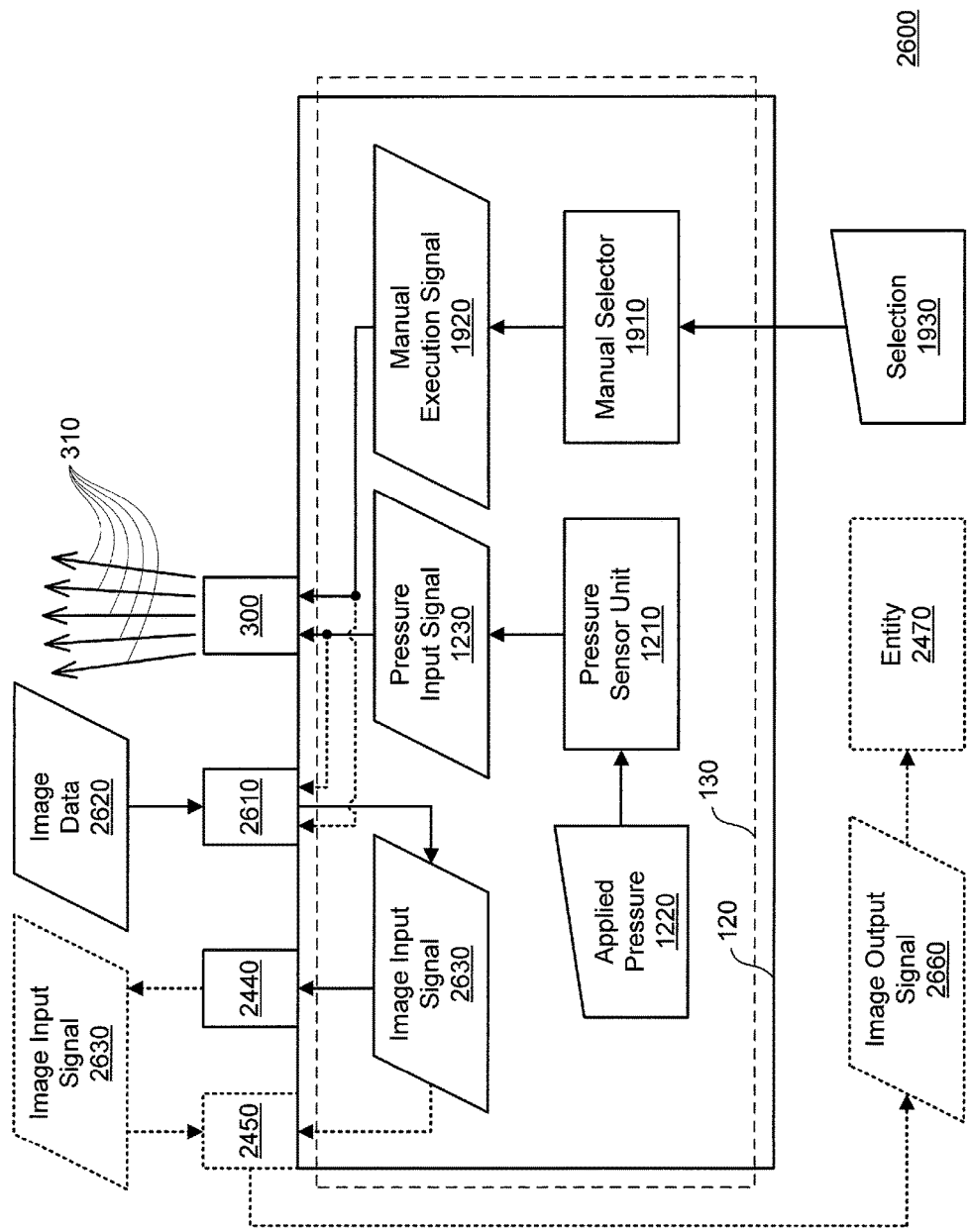
FIG. 26 is a diagram of a thirteenth exemplary self-defense system in accordance with an embodiment.

With reference now to FIG. 26, a thirteenth exemplary self-defense system 2600 in accordance with an embodiment is shown. Thirteenth exemplary self-defense system 2600 includes or comprises an image input unit 2610 (e.g., a digital camera) positioned to capture image data 2620 as a result of pressure input signal 1230 or manual execution signal 1920 by sensing image data 2620 and generating an image input signal 2630 based on or associated with image data 2620. Thirteenth exemplary self-defense system 2600 also includes or comprises a storage unit 2440 associated with image input unit 2610 and positioned to store image input signal 2630.

Furthermore, in an embodiment, thirteenth exemplary self-defense system 2600 optionally includes or comprises a transmitter 2450 associated with image input unit 2610 and positioned to automatically generate an image output signal 2660 corresponding to image input signal 2630 and automatically transmit image output signal 2660 to a preselected entity 2470. It is noted that transmitter 2450 may be configured to receive image input signal 2630 from either image input unit 2610 or storage unit 2440.

With reference now to FIGS. 27A and 27B, seventh and eighth exemplary logic systems 2700, 2701 in accordance with a number of exemplary embodiments are shown. Seventh and eighth exemplary logic systems 2700, 2701 are substantially similar to first and second exemplary logic systems 2000, 2001, respectively (see the discussions above regarding FIGS. 20A and 20B). However, in accordance with an embodiment, execution signal 510 may be implemented to cause image input unit 2610 to initiate a defense event. Indeed, one embodiment provides that execution signal 510 causes both projector unit 160 and image input unit 2610 to initiate a defense event at approximately the same time.

Figure 28:
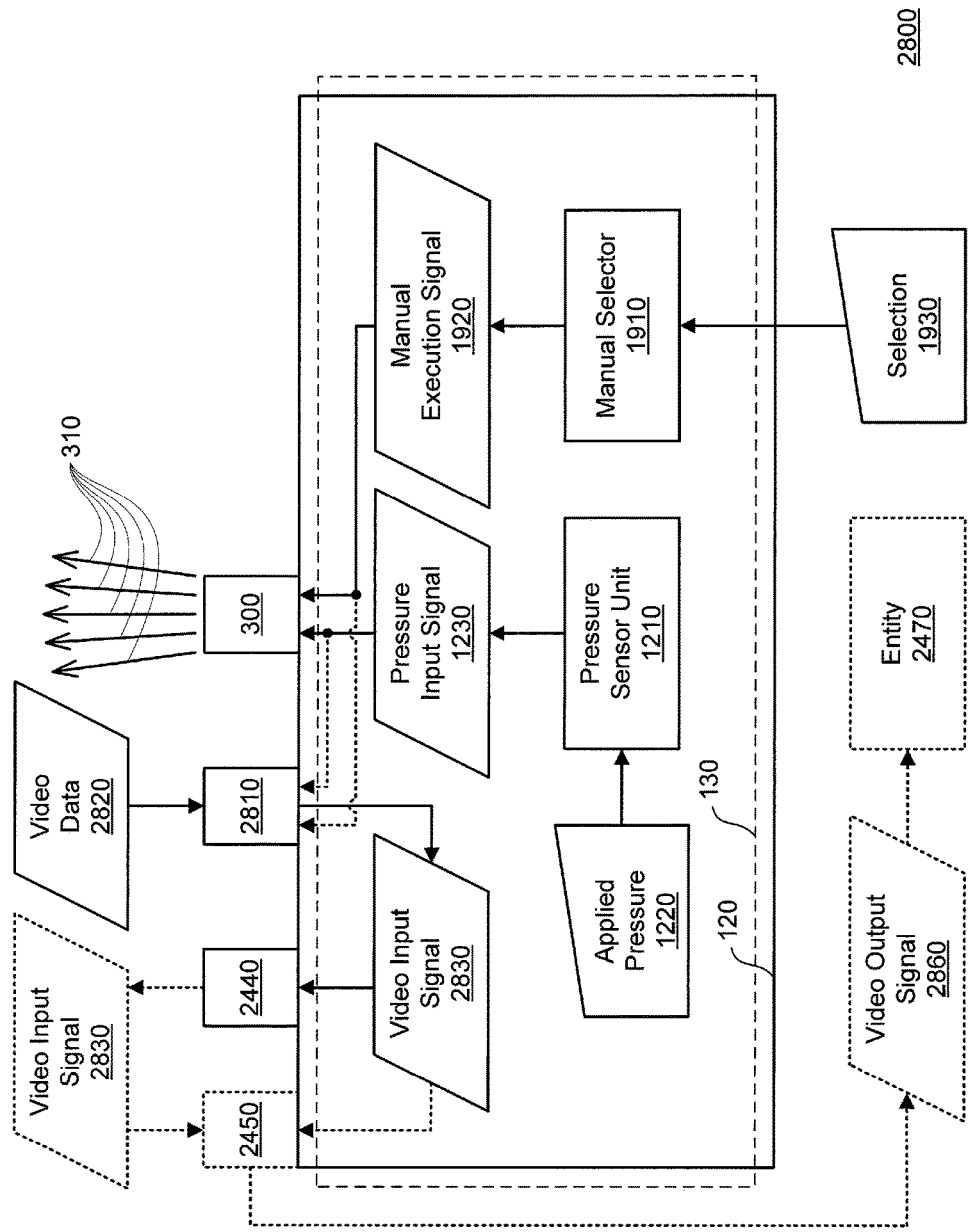
FIG. 28 is a diagram of a fourteenth exemplary self-defense system in accordance with an embodiment.

With reference now to FIG. 28, a fourteenth exemplary self-defense system 2800 in accordance with an embodiment is shown. Fourteenth exemplary self-defense system includes or comprises a video input unit 2810 (e.g., a digital camera with digital video recording capabilities) positioned to capture video data 2820 as a result of pressure input signal 1230 or manual execution signal 1920 by sensing video data 2820 and generating a video input signal 2830 based on or associated with video data 2820. Fourteenth exemplary self-defense system also includes or comprises a storage unit 2440 associated with video input unit 2810 and positioned to store video input signal 2830.

Furthermore, in an embodiment, fourteenth exemplary self-defense system 2800 optionally includes or comprises a transmitter 2450 associated with video input unit 2810 and positioned to automatically generate a video output signal 2860 corresponding to video input signal 2830 and automatically transmit video output signal 2860 to a preselected entity 2470. It is noted that transmitter 2450 may be configured to receive video input signal 2830 from either video input unit 2810 or storage unit 2440.

With reference now to FIGS. 29A and 29B, ninth and tenth exemplary logic systems 2900, 2901 in accordance with a number of exemplary embodiments are shown. Ninth and tenth exemplary logic systems 2900, 2901 are substantially similar to first and second exemplary logic systems 2000, 2001, respectively (see the discussions above regarding FIGS. 20A and 20B). However, in accordance with an embodiment, execution signal 510 may be implemented to cause video input unit 2810 to initiate a defense event. Indeed, one embodiment provides that execution signal 510 causes both projector unit 160 and video input unit 2810 to initiate a defense event at approximately the same time.

Figure 30:
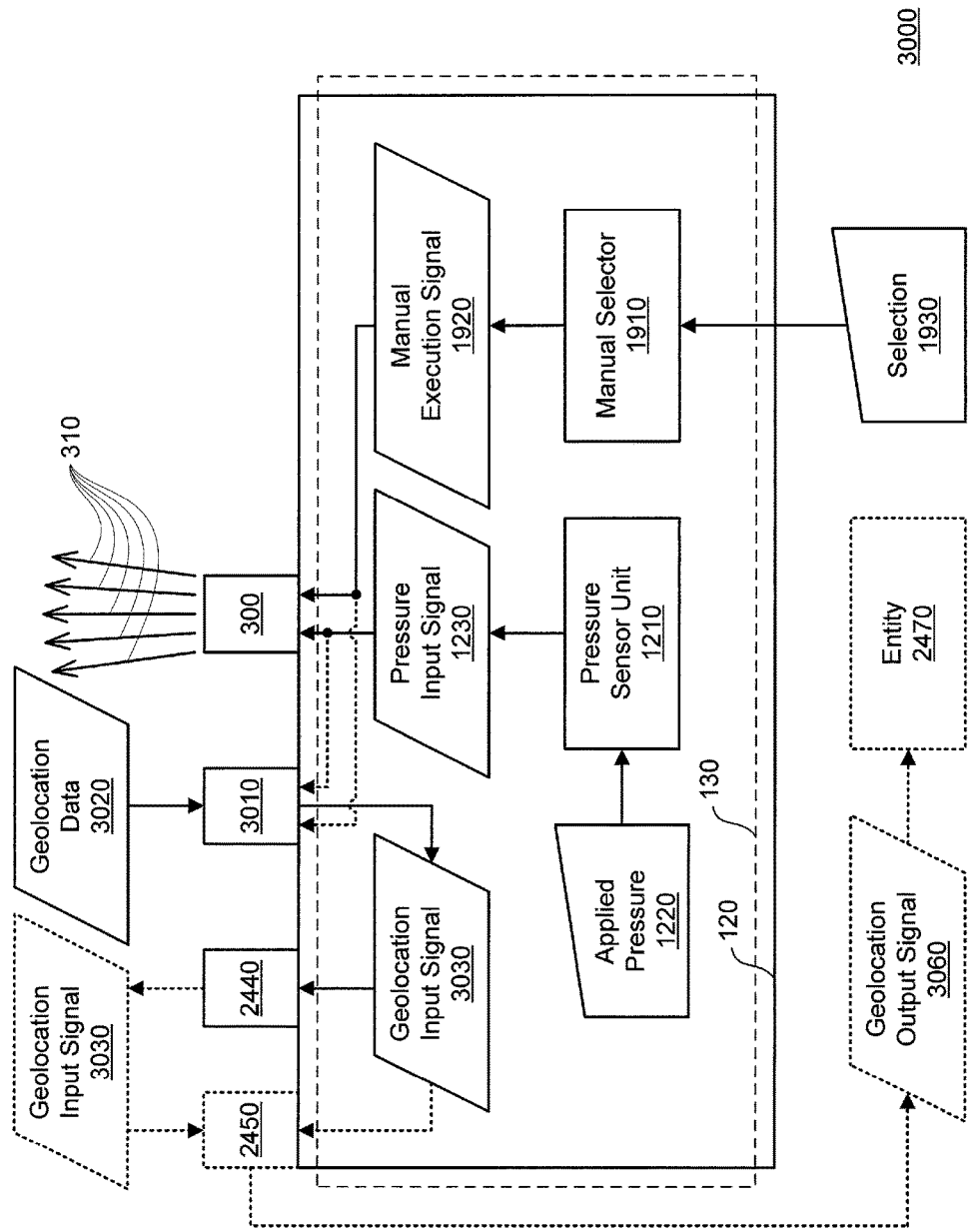
FIG. 30 is a diagram of a fifteenth exemplary self-defense system in accordance with an embodiment.

With reference now to FIG. 30, a fifteenth exemplary self-defense system 3000 in accordance with an embodiment is shown. Fifteenth exemplary self-defense system 3000 includes or comprises a geolocation unit 3010 positioned to sense geolocation data 3020 as a result of pressure input signal 1230 or manual execution signal 1920, calculate a geographic position (e.g., a geographic location corresponding to a current position of geolocation unit 3010) based on geolocation data 3020, and generate a geolocation input signal 3030 indicating the geographic position. In one embodiment, geolocation unit 3010 utilizes global positioning system (GPS) technology to calculate a geographic position. However, other geolocation paradigms may be implemented.

With reference still to FIG. 30, fifteenth exemplary self-defense system 3000 also includes or comprises a storage unit 2440 associated with geolocation unit 3010 and positioned to store geolocation input signal 3030. Furthermore, in an embodiment, fifteenth exemplary self-defense system 3000 optionally includes or comprises a transmitter 2450 associated with geolocation unit 3010, wherein transmitter 2450 is configured and positioned to automatically generate a geolocation output signal 3060 corresponding to geolocation input signal 3030 and automatically transmit geolocation output signal 3060 to a preselected entity 2470.

Figure 31A:
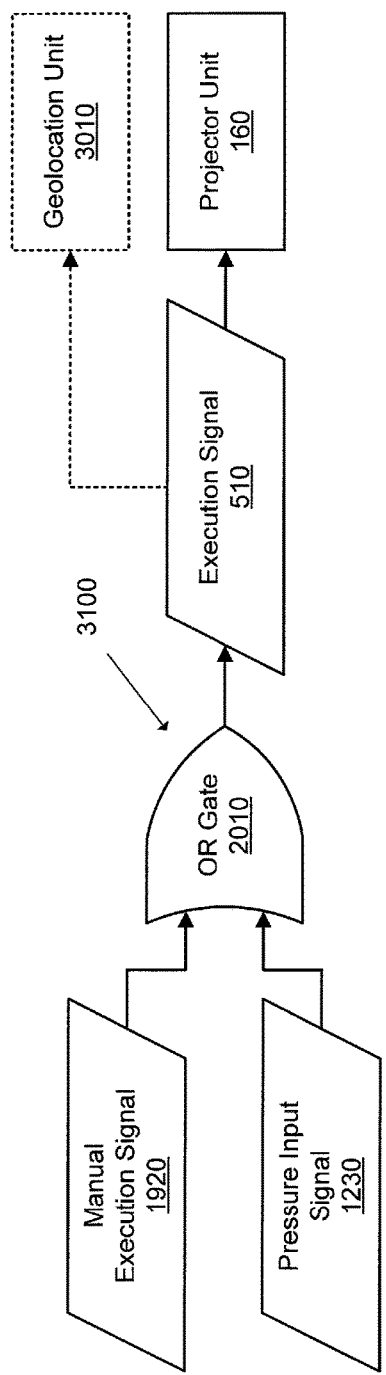
FIG. 31A is a diagram of an eleventh exemplary logic system in accordance with an embodiment.
Figure 31B:
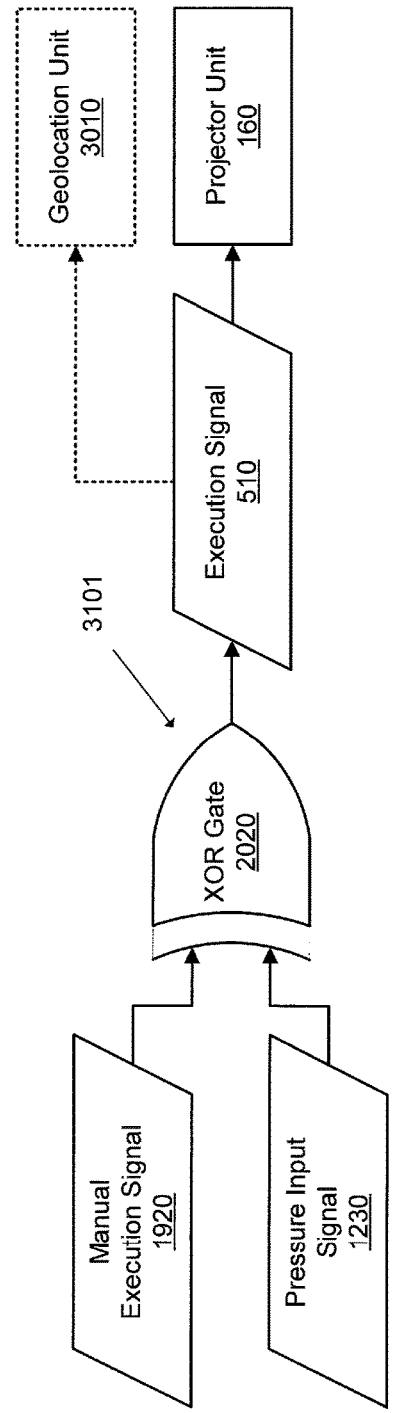
FIG. 31B is a diagram of a twelfth exemplary logic system in accordance with an embodiment.

With reference now to FIGS. 31A and 31B, eleventh and twelfth exemplary logic systems 3100, 3101 in accordance with a number of exemplary embodiments are shown. Eleventh and twelfth exemplary logic systems 3100, 3101 are substantially similar to first and second exemplary logic systems 2000, 2001, respectively (see the discussions above regarding FIGS. 20A and 20B). However, in accordance with an embodiment, execution signal 510 may be implemented to cause geolocation unit 3010 to initiate a defense event. Indeed, one embodiment provides that execution signal 510 causes both projector unit 160 and geolocation unit 3010 to initiate a defense event at approximately the same time.

Pursuant to one exemplary implementation, a self-defense system is integrated with an alarm unit, such as to scare an attacker into halting an attack, or at least lowering a degree of aggression associated with the attack, and possibly also attracting attention to an attack such that third-parties may intervene. To illustrate, and with reference now to FIG. 32, a sixteenth exemplary self-defense system 3200 in accordance with an embodiment is shown. Sixteenth exemplary self-defense system 3200 includes or comprises a storage unit 2440 configured to store preselected audio data 3210, such as audio data corresponding to a preselected audio alarm signal. Sixteenth exemplary self-defense system 3200 also includes or comprises an audio output unit 3220 (e.g., an audio speaker) associated with storage unit 2440 and configured to access preselected audio data 3210 based on pressure input signal 1230 or manual execution signal 1920. Audio output unit 3220 is also configured to generate and output an audio signal 3230 (e.g., an emergency siren) based on or associated with preselected audio data 3210.

Indeed, an embodiment provides that a sound frequency associated with audio signal 3230 is selected based on a hearing range associated with a potential attacker. Consider the example where a defense system as described herein is specifically designed to be worn by a jogger who could possibly be attacked by a dog when exercising outside. In so much as the dog may have a hearing range of approximately 40 hertz (Hz) to 60 kilohertz (kHz), which is much different than an average human hearing range of approximately 20 Hz to 20 kHz, audio signal 3230 is configured to have a sound frequency between 20 kHz and 60 kHz such that the alarm will function as a "dog whistle" specifically configured to disorientate the attacking dog without bothering human bystanders. However, in so much as it may be helpful to alert human bystanders to an attack, one embodiment provides that at least one audio frequency associated with audio signal 3230 is within a range of approximately 20 Hz to 20 kHz.

Figure 32:
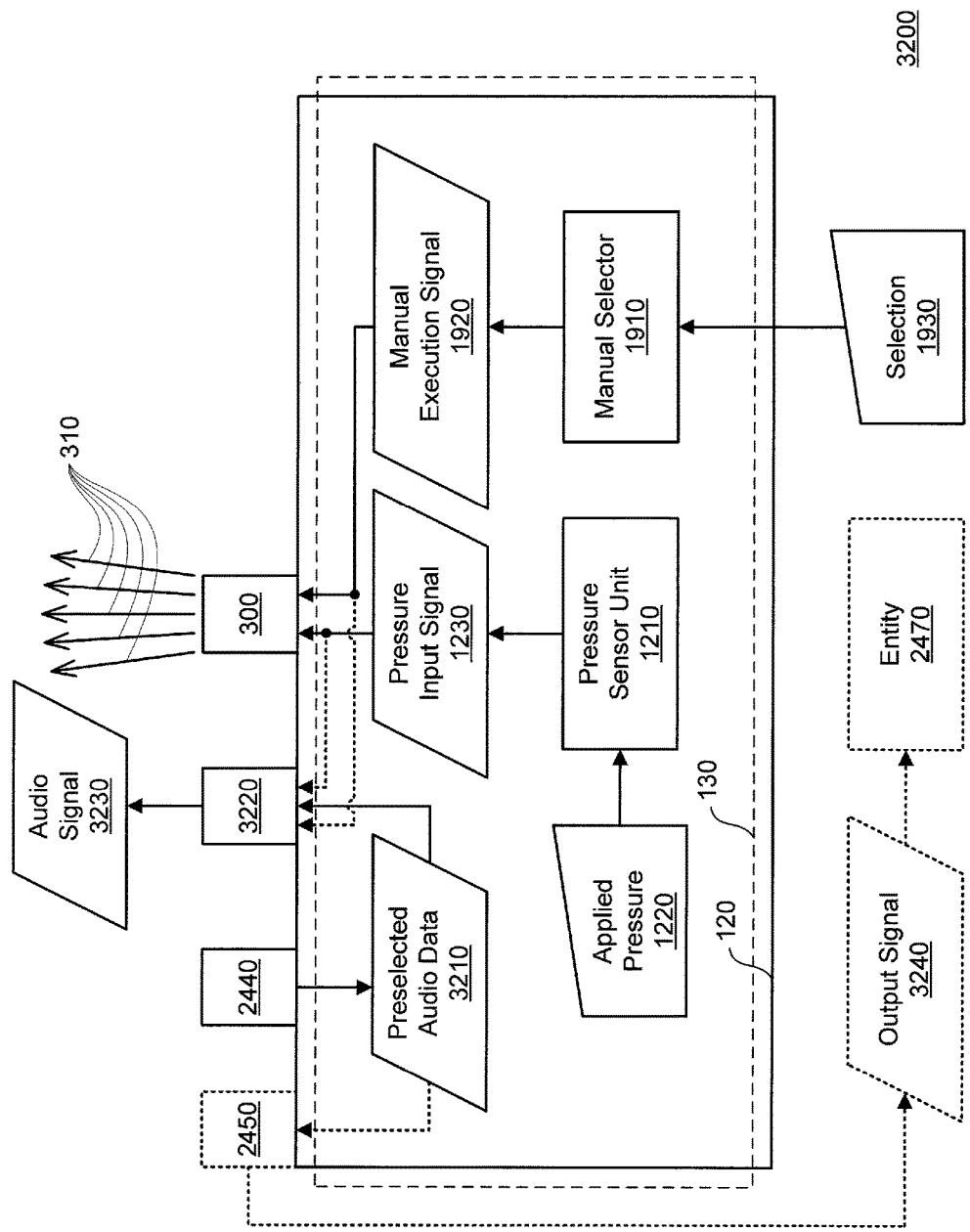
FIG. 32 is a diagram of a sixteenth exemplary self-defense system in accordance with an embodiment.

Furthermore, and with reference still to FIG. 32, a transmitter 2450 may optionally be implemented to automatically generate an output signal 3240 in response to the initiation of a defense event and automatically transmit output signal 3240 to a preselected entity 2470, such as a local law enforcement agency or emergency medical responder. It is noted that output signal 3240 may contain audio, image, video and/or geolocation data associated with a defense event, such as by combining a number of elements of sixteenth exemplary self-defense system 3200 with a number of elements of twelfth, thirteenth, fourteenth and/or fifteenth exemplary self-defense systems 2400, 2600, 2800, 3000.

Figure 33A:
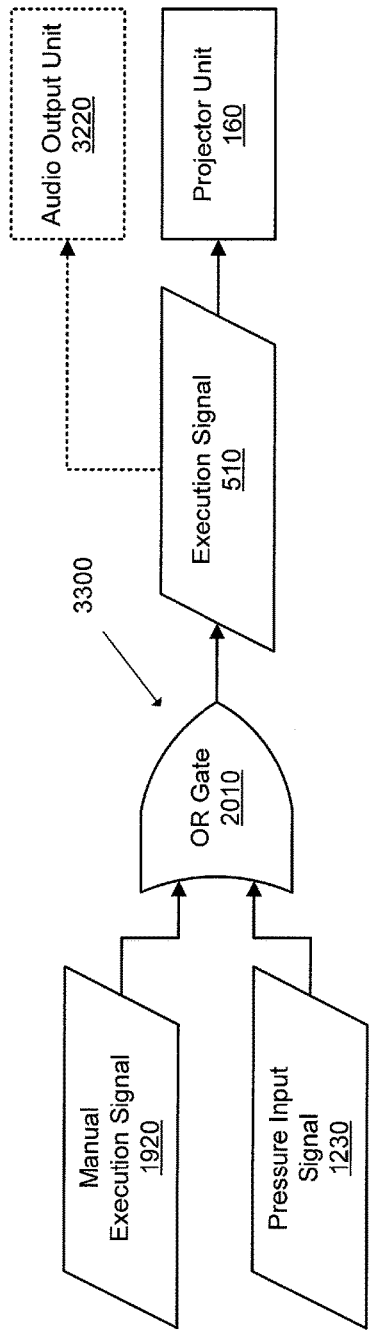
FIG. 33A is a diagram of a thirteenth exemplary logic system in accordance with an embodiment.
Figure 33B:
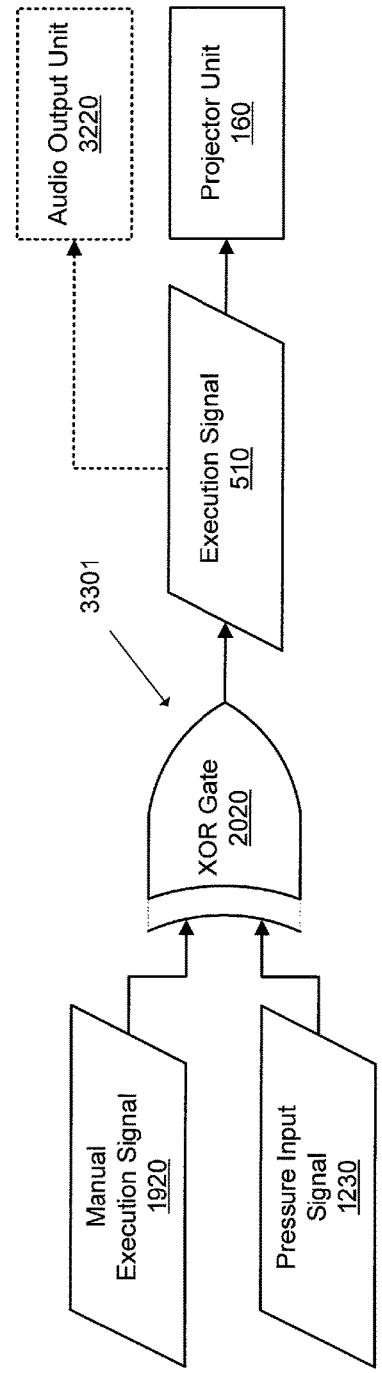
FIG. 33B is a diagram of a fourteenth exemplary logic system in accordance with an embodiment.

With reference now to FIGS. 33A and 33B, thirteenth and fourteenth exemplary logic systems 3300, 3301 in accordance with a number of exemplary embodiments are shown. Thirteenth and fourteenth exemplary logic systems 3300, 3301 are substantially similar to first and second exemplary logic systems 2000, 2001, respectively (see the discussions above regarding FIGS. 20A and 20B). However, in accordance with an embodiment, execution signal 510 may be implemented to cause audio output unit 3220 to initiate a defense event. Indeed, one embodiment provides that execution signal 510 causes both projector unit 160 and audio output unit 3220 to initiate a defense event at approximately the same time.

Various exemplary defense arrangements will now be explored, wherein these exemplary defense arrangements may include or be integrated with a number of defense devices discussed herein. However, the present technology is not limited to these exemplary arrangements. Indeed, other arrangements may be implemented.

Figure 34:
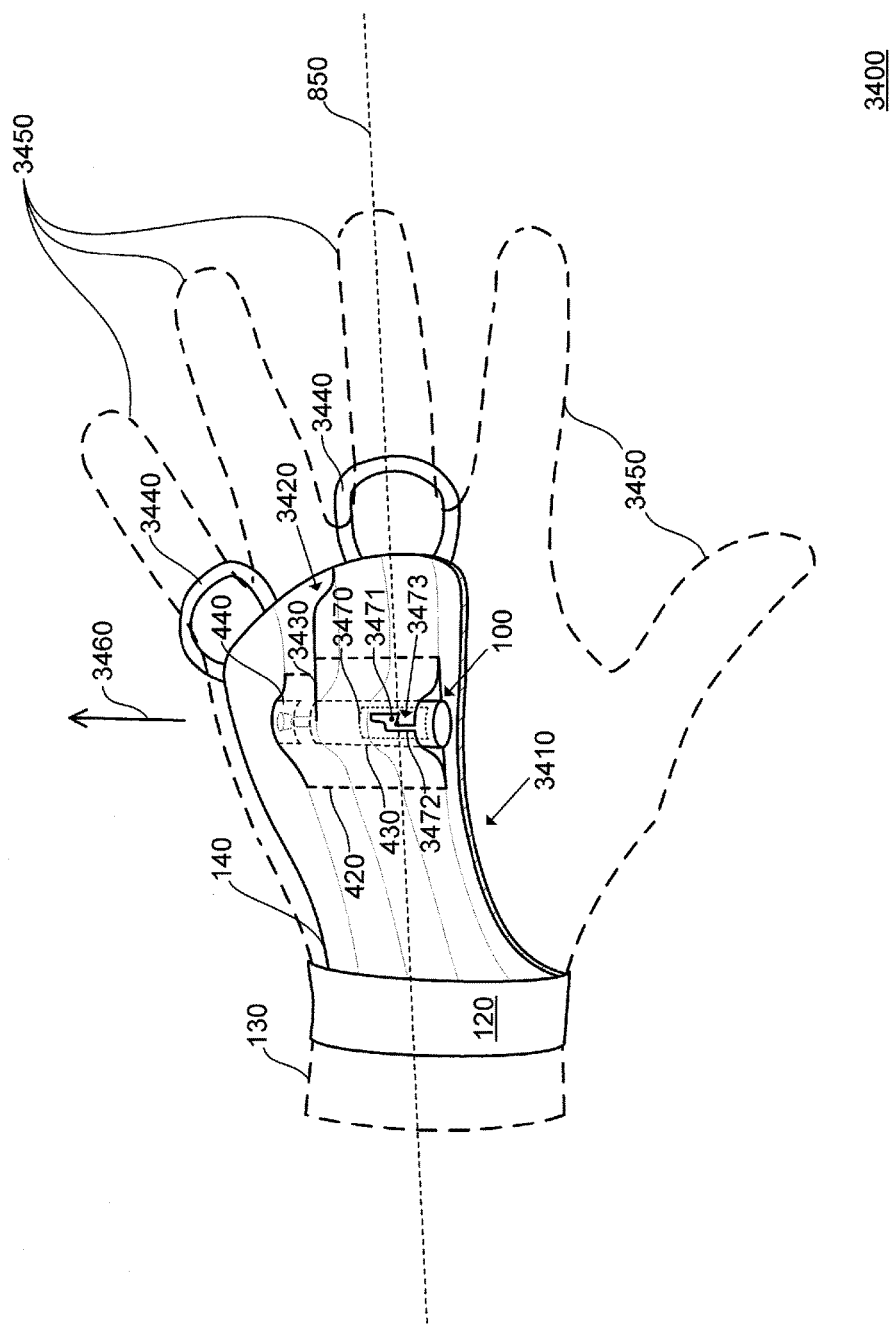
FIG. 34 is a diagram of a second exemplary defense arrangement in accordance with an embodiment.

With reference now to FIG. 34, a second exemplary defense arrangement 3400 in accordance with an embodiment is shown. In particular, a self-defense system 3410 includes or comprises a material 120, such as a wristband, sized to conform to appendage 130. Self-defense system 3410 also includes or comprises a defense unit 140 coupled with material 120, wherein defense unit 140 may be positioned on the back side of a user's hand (e.g., opposite the hand's palm region) such that the user's hand remains unencumbered to grasp items when self-defense system 3410 is being worn.

It is noted that material 120 is shown in FIG. 34 as being wrapped around a user's left-hand wrist. It is further noted that material 120 may be shaped differently than shown, such as where material 120 is a glove positioned between the user's hand and defense unit 140. However, it may be beneficial for the size of material 120 to be minimized, such as shown in FIG. 34, so as to decrease the amount of material applied to the user's hand and arm to thereby increase a degree of comfort associated with self-defense system 3410.

With reference still to FIG. 34, defense unit 140 includes or comprises a nozzle 440 sized to engage a container 430 that is configured to contain a substance under pressure. Nozzle 440 is positioned to release an amount of the substance from container 430 in a discharging direction 3460 in response to a movement of container 430 in a direction toward nozzle 440.

To further illustrate, and with reference to the exemplary implementation shown in FIG. 34, defense unit 140 includes, comprises or is integrated with (1) nozzle 440 and (2) a housing 420 sized to house container 430. For example, defense unit 140 may be fabricated from a single piece of material, such as an injection molded carbon or plastic material, wherein housing 420 is formed within this same piece of material (so that a chamber is formed in defense unit 140 that is sized to receive container 430, such as shown in FIG. 34). Additionally, nozzle 440 is integrated with, or formed within, this same piece of material. In this manner, self-defense system 3410 may be fabricated with a relatively small cost per unit while offering a comfortable and effective self-defense paradigm.

With reference still to FIG. 34, in an embodiment, defense unit 140 optionally includes or comprises an appendage anchor 3420 sized to receive a first digit so as to anchor a second digit relative to nozzle 440 and enable the second digit to manually push container 430 toward nozzle 440. For example, when defense unit 140 is positioned on a user's left hand, as shown, the user anchors his or her right-hand index finger on appendage anchor 3420 and pushes container 430 toward nozzle 440 with his or her right-hand thumb. In this manner, appendage anchor 3420 is implemented to minimize a movement of defense unit 140 relative to appendage 130 when force is applied to container 430 to thereby achieve a degree of leverage on container 430.

Indeed, one embodiment provides that appendage anchor 3420 includes or comprises a digit receiver or brace 3430 positioned outside a palm region of appendage 130 when the second digit manually pushes container 430 relative to nozzle 440. Consider the example where defense unit 140 is mounted on the back of a user's left hand, opposite the user's left-hand palm region. Digit receiver or brace 3430 includes or comprises a piece of material extending from housing 420, nozzle 440 or defense unit 140, which may define a finger receptacle within defense unit 140. The user anchors his or her right-hand index finger on digit receiver or brace 3430, such as by positioning the index finger within the finger receptacle, and pushes container 430 toward nozzle 440 with his or her right-hand thumb.

Thus, it is noted that defense unit 140 may be shaped to enable a user to increase a degree of manual leverage on container 430. In one embodiment, one or more appendage braces 3440 are optionally coupled or integrated with defense unit 140. One or more appendage braces 3440 are sized to conform to or wrap around one or more other appendages 3450 so as to anchor defense unit 140 and nozzle 440 relative to one or more other appendages 3450. For example, when defense unit 140 is positioned on a user's left hand, as shown, one or more appendage braces 3440 are wrapped around one or more other appendages 3450, as shown. It is noted that defense unit 140 is anchored to the user's left arm by material 120, and that also anchoring defense unit 140 to one or more other appendages 3450 enables the user to achieve an additional degree of leverage on container 430 because the degree to which defense unit 140 moves relative to appendage 130 when the user pushes on container 430 with his or her right hand will be minimized.

Moreover, in an embodiment, one or more appendage braces 3440, as well as appendage anchor 3420, are implemented to help maximize the degree of leverage that may be achieved. Pursuant to one embodiment, however, material 120 is itself sized and configured to wrap around both the user's wrist and one or more other appendages 3450 such that one or more appendage braces 3440 may or may not be implemented, depending on how much additional support and leverage is to be provided.

With reference still to FIG. 34, it is noted that nozzle 440 is positioned to release an amount of the substance from container 430 in a discharging direction 3460 in response to a movement of container 430 in a direction toward nozzle 440. In accordance with an embodiment, discharging direction 3460 is substantially perpendicular to an axis corresponding to a longest length of appendage 130 (as represented by major length axis 850), although one embodiment provides that discharging direction 3460 is angled approximately 45 degrees or more (e.g., approximately 60 degrees) away from this axis. It is noted that such an arrangement may increase an effectiveness of a defense event, such as when users naturally position their arms in front of their faces in a defensive posture such that projecting a substance in the selected direction causes the substance to be projected toward the oncoming attacker without necessitating a change in the natural, defensive posture of the users. It is further noted that discharging direction 3460 may be selected based on a probable angle of attack of a potential attacker with respect to this defensive posture.

Furthermore, an embodiment provides that a locking mechanism 3470 may be optionally implemented to prevent container 430 from accidentally sliding out of housing 420. For example, as shown in FIG. 34, an extension 3471 is coupled with or extends from container 430, wherein extension 3471 is sized to slide or be repositioned through a path 3472 formed in housing 420 until extension 3471 engages a notch 3473 sized to hold extension 3471 in place. In this manner, container 430 is unable to slide out of housing 420 unless extension 3471 is manually removed from notch 3473 and slid out of path 3472. It is noted, however, that the present technology is not limited to this type of locking mechanism, and that other types of locking mechanisms may be implemented.

Figure 35A:
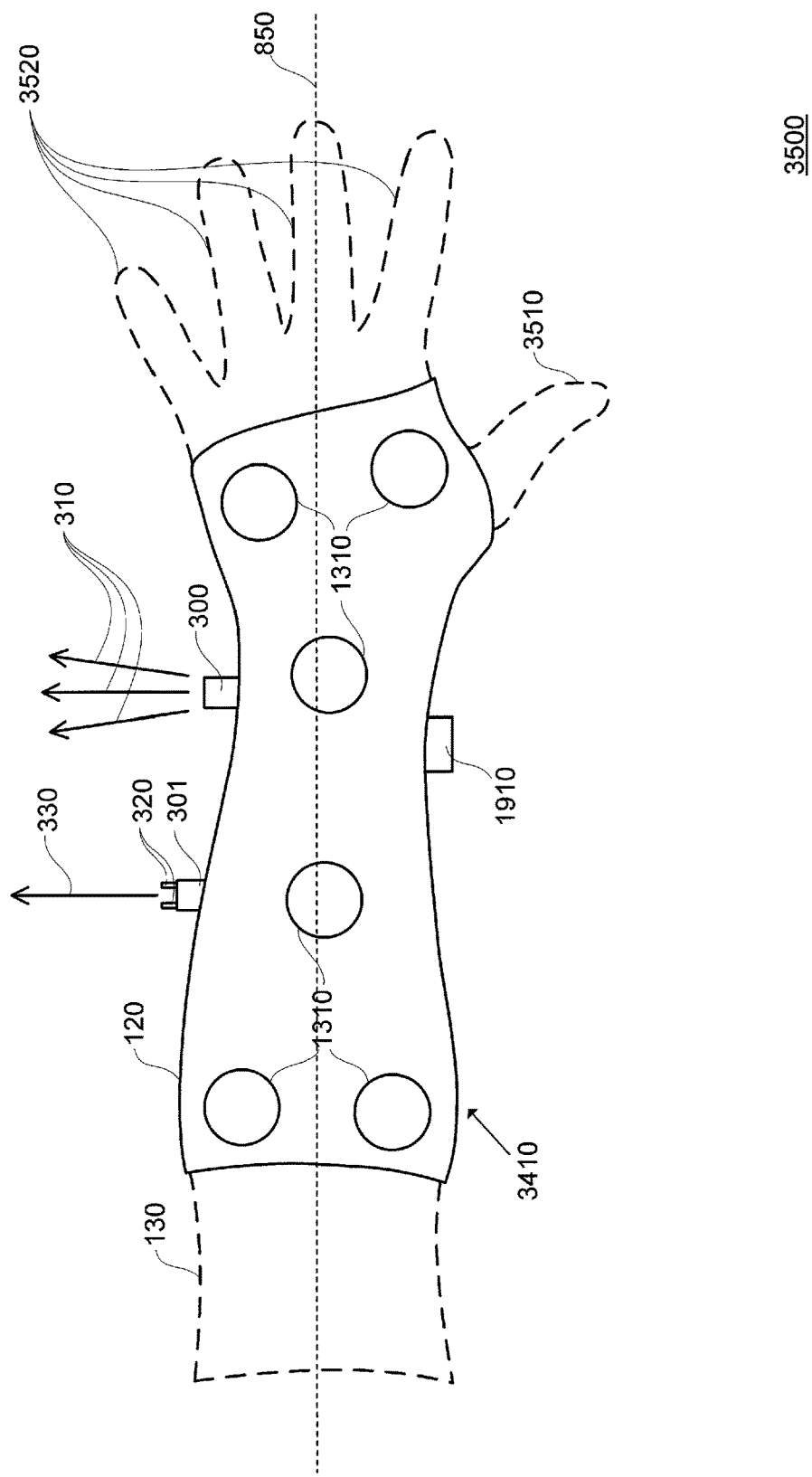
FIGS. 35A and 35B are diagrams of a third exemplary defense arrangement in accordance with an embodiment.
Figure 35B:
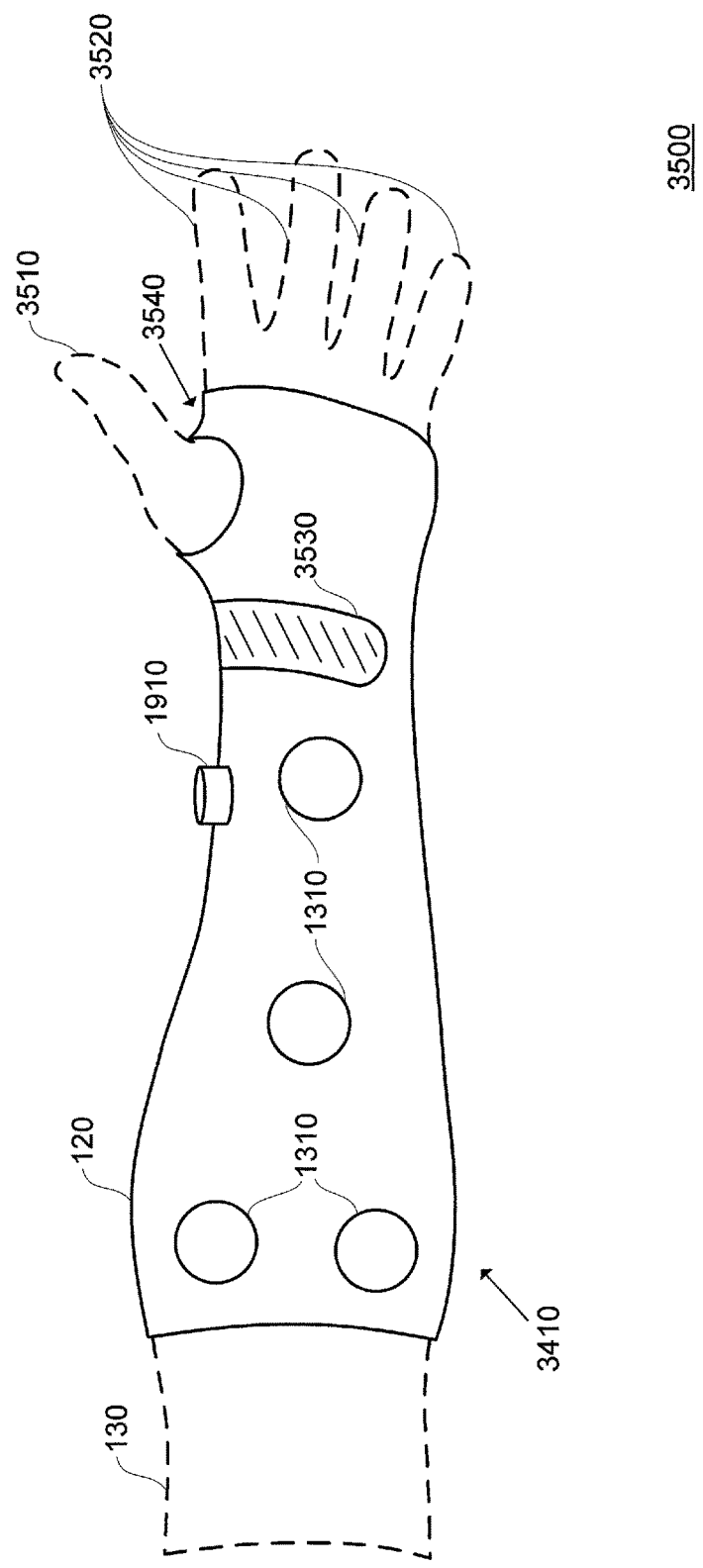

With reference now to FIGS. 35A and 35B, a third exemplary defense arrangement 3500 in accordance with an embodiment is shown. In particular, an appendage 130 is shown, wherein appendage 130 includes or comprises a user's left hand and forearm. Additionally, a self-defense system 3410 is shown, wherein self-defense system 3410 includes or comprises a material 120 configured to wrap around the user's left hand and forearm. Self-defense system 3410 also includes or comprises one or more self-defense devices, such as projector unit 300 and/or conductive energy device 301. Alternatively, or in addition to the foregoing, other types of defense devices may be implemented.

In an embodiment, self-defense system 3410 also includes or comprises a manual selector 1910 integrated with one or more of the implemented self-defense devices. Consider the example where manual selector 1910 includes or comprises an electronic button that causes projector unit 300 and/or conductive energy device 301 to initiate a defense event when the button is pushed. When the user is assaulted by an attacker, the user instinctively raises his arms in front of his face in a defensive posture, which in turn causes the button to be positioned between the user's face and his left arm. The user now has the option of simply pressing the button with his right hand to thereby manually initiate a defense event, without compromising the user's natural, defensive posture due to the alignment of one or more of the implemented self-defense devices with a direction of attack of the oncoming attacker.

In one embodiment, self-defense system 3410 includes or comprises a number of pressure sensors 1310 integrated with one or more of the implemented self-defense devices. Consider the example where each of pressure sensors 1310 is configured to sense an applied pressure, such as when an attacker grabs the user's left arm. In response to one or more of these sensors sensing the applied pressure, projector unit 300 and/or conductive energy device 301 automatically initiate a defense event. In this manner, the user, when attacked, can simply retreat to a natural, defensive posture, wherein the user's arms are in front of the user's face, and a defense event will be automatically executed based on the attacker's actions such that the user is not forced to manually initiate the defense event.

In accordance with an embodiment, self-defense system 3410 includes or comprises one or more appendage braces 3440. To illustrate, and with reference still to FIG. 35B, it is noted that a portion 3540 of material 120 wraps around the base of one of the user's digits 3510 (e.g., the user's thumb) such that material 120 is braced or anchored relative to digit 3510. In this manner, a rotation of material 120 relative to appendage 130 is precluded, such that the positions of (1) manual selector 1910 relative to the user's face and (2) projector unit 300 and/or conductive energy device 301 relative to an oncoming attacker, respectively, can be maintained. Alternatively, or in addition to the foregoing, material 120 may be sized to anchor with one or more other digits 3520 (e.g., the user's fingers).

Furthermore, pursuant to one embodiment, material 120 includes, comprises or is integrated with one or more size adjustors, such as strap 3530, configured to be adjusted so as to resize a fit of material 120. In this manner, material 120 may be adjusted to fit users of different sizes, as well as to tighten material 120 around appendage 130 once self-defense system 3410 has been adequately positioned and aligned.

Exemplary Communication Arrangements

Pursuant to an exemplary implementation, various components or modules of the present technology may communicate with one another, such as by routing the various signals discussed herein, using physical transmission lines or data busses. However, one embodiment provides that such information may be wirelessly routed.

With reference now to FIG. 36A, a first exemplary communication arrangement 3600 in accordance with an embodiment is shown, wherein a signal is to be routed from a source 3610 to a destination 3620. First, the information is routed from source 3610 to a router 3630 through a first transmission line 3640. Subsequently, this information is routed from router 3630 to a receiver 3650 through a second transmission line 3660. Finally, the information is routed from receiver 3650 to destination 3620 through a third transmission line 3670. It is noted that these transmission lines may be, for example, copper wires or fiber optic lines. It is further noted that information may also be routed over the Internet and/or through a distinguishable intranet.

With reference now to FIG. 36B, a second exemplary communication arrangement 3601 in accordance with an embodiment is shown, wherein a signal is to be routed from source 3610 to destination 3620. First, the information is routed from source 3610 to a wireless transmitter 3680 through first transmission line 3640. Subsequently, this information is wirelessly routed from wireless transmitter 3680 to a wireless receiver 3690, such as using radio waves and/or a wireless communication network. Finally, the information is routed from wireless receiver 3690 to destination 3620 through second transmission line 3660. It is noted that various wireless communication methods may be implemented, such as by short wavelength radio transmissions (e.g., Bluetooth™ transmissions) or across cellular networks, and that the present technology is not limited to any particular wireless communication methodology.

Exemplary Computer System Environment

It is noted that various components of the present technology may be hard-wired or configured to carry out various actions and operations discussed herein. Pursuant to one embodiment, however, a computer system may be implemented to carry out various operations.

Figure 37:
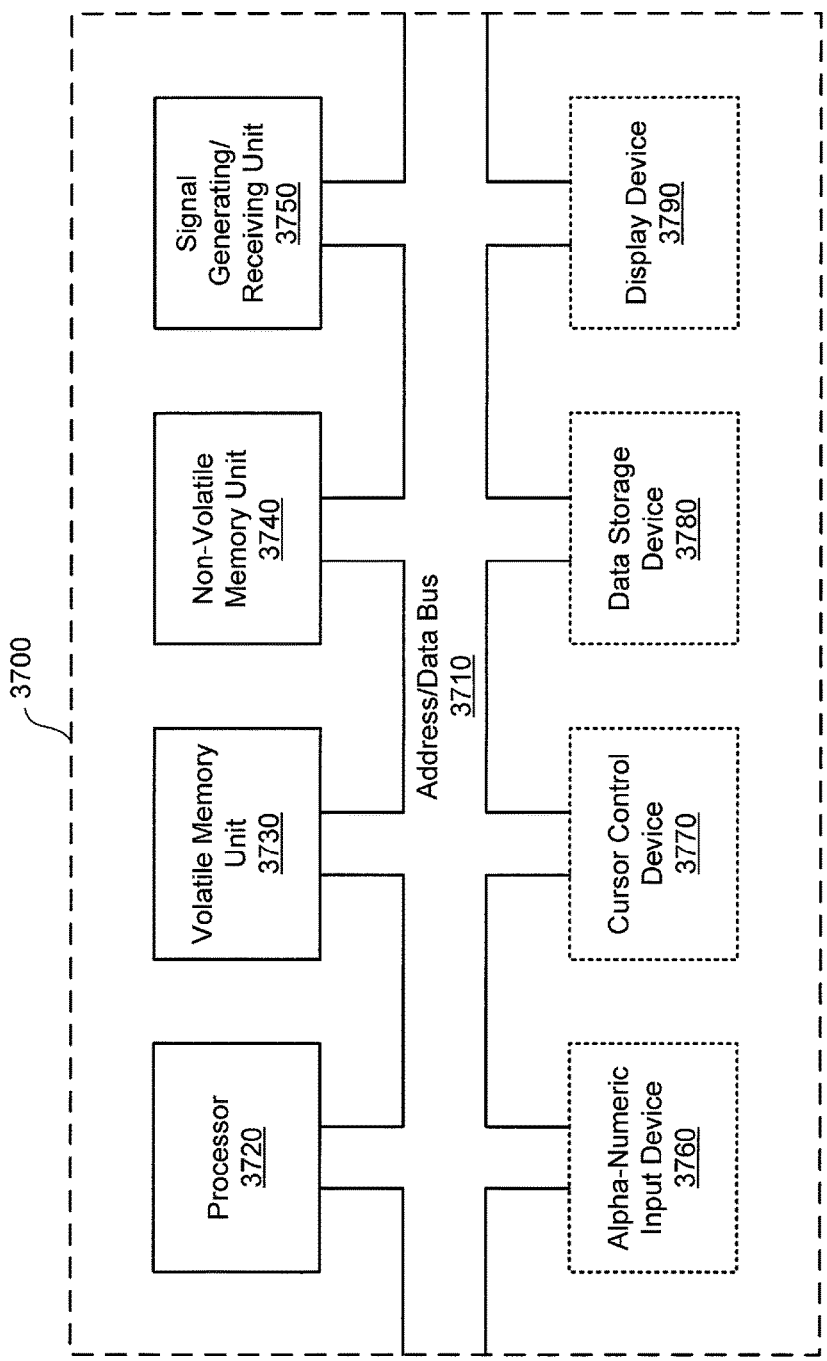
FIG. 37 is a diagram of an exemplary computer system in accordance with an embodiment.

With reference now to FIG. 37, an exemplary computer system 3700 in accordance with an embodiment is shown. Computer system 3700 may be any type of computing device (e.g., a computing device utilized to perform calculations, processes, operations, and functions associated with a program or algorithm). Within the discussions herein, certain processes and steps are discussed that are realized, pursuant to one embodiment, as a series of instructions, such as a software program, that reside within computer-readable memory units and are executed by one or more processors of computer system 3700. When executed, the instructions cause computer system 3700 to perform specific actions and exhibit specific behavior described in various embodiments herein.

With reference still to FIG. 37, computer system 3700 includes or comprises an address/data bus 3710 configured to communicate information between a source and a destination. In addition, one or more data processors, such as processor 3720, are coupled with address/data bus 3710, wherein processor 3720 is configured to process information and instructions. In an embodiment, processor 3720 is a microprocessor or microcontroller, although other types of data processors may be implemented.

Computer system 3700 also includes or comprises a number of data storage components, such as a volatile memory unit 3730 coupled with address/data bus 3710 and configured to store information and instructions for processor 3720, wherein volatile memory unit 3730 may include or comprise random access memory (RAM), such as static RAM and/or dynamic RAM. Moreover, computer system 3700 further includes or comprises a non-volatile memory unit 3740 coupled with address/data bus 3710 and configured to store static information and instructions for processor 3720. In an embodiment, non-volatile memory unit 3740 includes read-only memory (ROM), such as programmable ROM, flash memory, erasable programmable ROM (EPROM), and/or electrically erasable programmable ROM (EEPROM). The foregoing notwithstanding, it is noted that the present technology is not limited to the use of the exemplary storage units discussed herein, and that other types of memory may be implemented.

With reference still to FIG. 37, computer system 3700 also includes or comprises one or more signal generating and receiving devices, such as signal generating/receiving unit 3750, coupled with address/data bus 3710 and configured to enable computer system 3700 to interface with other electronic devices and computer systems. The communication interface(s) implemented by the one or more signal generating and receiving devices may utilize wired (e.g., serial cables, modems, and network adaptors) and/or wireless (e.g., wireless modems and wireless network adaptors) communication technologies.

In an embodiment, computer system 3700 optionally includes or comprises an alphanumeric input device 3760 coupled with address/data bus 3710, wherein alphanumeric input device 3760 includes or comprises alphanumeric and function keys for communicating information and command selections to processor 3720. Moreover, pursuant to one embodiment, a cursor control device 3770 is optionally coupled with address/data bus 3710, wherein optional cursor control device 3770 is configured to communicate user input information and command selections to processor 3720. For example, cursor control device 3770 may be implemented using a mouse, a track-ball, a track-pad, an optical tracking device, or a touch screen. In a second example, a cursor is directed and/or activated in response to input from alphanumeric input device 3760, such as when special keys or key sequence commands are executed. It is noted, however, that a cursor may be directed by other means, such as, for example, voice commands.

With reference still to FIG. 37, computer system 3700, pursuant to one embodiment, optionally includes or comprises a data storage device 3780 coupled with address/data bus 3710, wherein data storage device 3780 is configured to store information and/or computer-executable instructions. To illustrate, one example provides that data storage device 3780 is a magnetic or optical disk drive, such as a hard disk drive (HDD), a floppy disk drive, a compact disk ROM (CD-ROM) drive, or a digital versatile disk (DVD) drive.

Furthermore, in an embodiment, a display device 3790 is optionally coupled with address/data bus 3710 and configured to display video and/or graphics. Display device 3790 may be, for example, a cathode ray tube (CRT) display, a liquid crystal display (LCD), a field emission display (FED), a plasma display, or any other display device suitable for displaying video and/or graphic images and alphanumeric characters capable of being recognized by a user.

It is noted that computer system 3700 is presented as an exemplary computing environment in accordance with an embodiment. However, computer system 3700 is not strictly limited to being a computer system. For example, one embodiment provides that computer system 3700 represents a type of data processing analysis that may be used in accordance with various embodiments described herein. Moreover, other computing systems may also be implemented. Indeed, the present technology is not limited to any particular data processing environment.

Furthermore, although various embodiments discussed herein involve a series of specific steps, actions or operations for achieving a result, it is noted these steps, actions or operations are examples of various steps, actions or operations that may be performed in accordance with a number of exemplary implementations. Indeed, the embodiments disclosed herein may be configured such that various other steps, actions or operations are performed, such as variations of the steps, actions or operations recited. Moreover, the steps disclosed herein may be performed in an order different than presented, and not all of the steps are necessarily performed in a particular embodiment.

Exemplary Concepts

It is noted that the foregoing discussion has presented at least the following exemplary concepts:

Concept 1. A self-defense system including or comprising:
a defense unit configured to initiate a defense event in response to an input.

Concept 2. A self-defense system including or comprising:
a material sized to conform to an appendage; and
a defense unit coupled with the material and positioned to initiate a defense event in response to an input.

Concept 3. A self-defense system including or comprising:
a material sized to conform to an appendage; and
first and second projector units coupled with the material and positioned to project one or more substances in first and second directions, respectively.

Concept 4. The self-defense system of Concept 3, further including or comprising:
a projection initiator unit associated with the first and second projector units and configured to enable a projection of the one or more substances.

Concept 5. A self-defense system including or comprising:
a material sized to conform to an appendage; and
a projector unit coupled with the material at a coupling surface area and positioned to project a substance in a direction that is substantially normal to the coupling surface area and/or substantially perpendicular to an axis corresponding to a longest length of the appendage.

Concept 6. The self-defense system of Concept 5, further including or comprising:
a projection initiator unit associated with the projector unit and configured to enable a projection of the substance.

Although various exemplary embodiments of the present technology are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A self-defense system comprising:
a material sized to conform to an appendage; and
a defense unit coupled with the material,
wherein the defense unit comprises or is integrated with:
a housing sized to house a container configured to contain a substance under pressure; and
a nozzle sized to engage the container, the nozzle positioned to release an amount of the substance from the container in a discharging direction, and
wherein a locking mechanism is implemented to hold the container inside the housing, and
wherein one or more appendage braces are coupled with the defense unit, the one or more appendage braces sized to conform to or wrap around one or more other appendages, respectively, so as to anchor the nozzle relative to the one or more other appendages and thereby increase a degree of leverage that a user is able to exert on the container when the user is wearing the defense unit.

2. The self-defense system of claim 1, wherein the substance is a lachrymatory agent or pepper spray.

3. The self-defense system of claim 1, wherein the material is a wristband configured to wrap around a wrist.

4. The self-defense system of claim 1, wherein the material is shaped to be worn as a glove positioned between a hand and the defense unit.

5. The self-defense system of claim 1, wherein the material comprises cloth, rubber or neoprene.

6. A self-defense system comprising:
a material sized to conform to an appendage; and
a defense unit coupled with the material;
wherein the defense unit comprises or is integrated with:
a housing sized to house a container containing a substance; and
a nozzle sized to engage the container, the nozzle positioned to release an amount of the substance from the container in a discharging direction, and
wherein one or more appendage braces are coupled with the defense unit, the one or more appendage braces sized to conform to or wrap around one or more other appendages, respectively.

7. The self-defense system of claim 6, wherein the substance is a lachrymatory agent or pepper spray.

8. The self-defense system of claim 6, wherein the material is a wristband configured to wrap around a wrist.

9. The self-defense system of claim 6, wherein the material comprises cloth, rubber or neoprene.

10. The self-defense system of claim 6, wherein the defense unit is configured to be worn on a back side of a hand, opposite a palm region of the hand.

11. A self-defense system comprising:
a material sized to conform to an appendage; and
a defense unit coupled with the material;

wherein the defense unit comprises or is integrated with:
- a housing sized to house a container containing a substance; and
- a nozzle sized to engage the container, the nozzle positioned to release an amount of the substance from the container in a discharging direction, wherein a locking mechanism is implemented to hold the container inside the housing, and wherein the nozzle is configured to release the amount of the substance from the container in the discharging direction in response to a movement of the container in a direction toward the nozzle.

12. The self-defense system of claim 11, wherein the substance is a lachrymatory agent or pepper spray.

13. The self-defense system of claim 11, wherein the material is a wristband configured to wrap around a wrist.

14. The self-defense system of claim 11, wherein the material is shaped to be worn as a glove positioned between a hand and the defense unit, and
- wherein the defense unit is configured to be worn on a back side of the hand, opposite a palm region of the hand.

15. The self-defense system of claim 11, further comprising:
- one or more appendage braces coupled with the defense unit, the one or more appendage braces sized to conform to or wrap around one or more other appendages, respectively, so as to anchor the nozzle relative to the one or more other appendages and thereby increase a degree of leverage that a user is able to exert on the container when the user is wearing the defense unit.

16. The self-defense system of claim 1, wherein the nozzle is configured to release the amount of the substance from the container in the discharging direction in response to a movement of the container in a direction toward the nozzle.

17. The self-defense system of claim 6, wherein the nozzle is configured to release the amount of the substance from the container in the discharging direction in response to a movement of the container in a direction toward the nozzle.

18. The self-defense system of claim 6, wherein a locking mechanism is implemented to hold the container inside the housing.

19. The self-defense system of claim 11, wherein the discharging direction, when the material is worn on the appendage, is one of:
- substantially perpendicular to an axis corresponding to a longest length of the appendage;
- angled approximately 60 degrees away from the axis corresponding to the longest length of the appendage; and
- angled approximately 45 degrees away from the axis corresponding to the longest length of the appendage.

20. The self-defense system of claim 11, wherein the defense unit is fabricated from an injection molded carbon or plastic material,
- wherein the nozzle is integrated with or formed within the injection molded carbon or plastic material,
- wherein the housing is formed within the injection molded carbon or plastic material such that a chamber is formed in the defense unit, and
- wherein the chamber is sized to receive the container.

* * * * *